(12) United States Patent
Humeau et al.

(10) Patent No.: US 6,627,442 B1
(45) Date of Patent: Sep. 30, 2003

(54) METHODS FOR STABLE TRANSDUCTION OF CELLS WITH HIV-DERIVED VIRAL VECTORS

(75) Inventors: Laurent Humeau, Gaithersburg, MD (US); Wei Han, Montgomery Village, MD (US); Xiaobin Lu, Gaithersburg, MD (US); Vladimir Slepushkin, Damascus, MD (US); Mechelle Lesher, Frederick, MD (US); Brian Davis, Gaithersburg, MD (US); Yung-Nien Chang, Cockeysville, MD (US); Boro Dropulic, Ellicott City, MD (US)

(73) Assignee: VIRxSYS Corporation, Gaithersburg, MD (US)

( * ) Notice: Subject to any disclaimer, the term of this patent is extended or adjusted under 35 U.S.C. 154(b) by 69 days.

(21) Appl. No.: 09/653,088

(22) Filed: Aug. 31, 2000

(51) Int. Cl.[7] .................. C12N 15/85; C12N 15/86; C12N 15/87; C12N 5/00; C12N 5/08; C12N 15/00
(52) U.S. Cl. .................. 435/455; 435/325; 435/372; 435/320.1
(58) Field of Search .................. 435/456, 459, 435/320.1, 455, 325, 366; 424/93.1, 93.2, 93.6

(56) References Cited

U.S. PATENT DOCUMENTS

| | | | |
|---|---|---|---|
| 5,512,421 A | | 4/1996 | Burns et al. |
| 5,739,018 A | | 4/1998 | Miyanohara et al. |
| 5,814,500 A | | 9/1998 | Dietz |
| 5,885,806 A | | 3/1999 | Dropulic et al. |
| 6,013,516 A | * | 1/2000 | Verma et al. |
| 6,060,317 A | * | 5/2000 | Malech |

FOREIGN PATENT DOCUMENTS

WO    WO 96/34970    11/1996

OTHER PUBLICATIONS

WF Anderson, Nature, "Human gene therapy," Apr. 1998, vol. 392, pp. 25–28.*
KA Miktrophanous et al., Gene Therapy, "Stable gene transfer to the nervous system using a non–primate lentiviral vector," 1999, 6, pp. 1808–1818.*
JH Richardson et al, Gene Therapy, "Intrabody–mediated knockout of the high–affinity IL–2 receptor in primary human T cells using a bicistronic lentivirus vector," 1998, 5, pp. 635–644.*
E Costello et al, Gene transfer into stimulated and unstimulated T lymphocytes by HIV–1–derived lentiviral vectors, Gene Therapy (2000) 7, 596–604.*
Movassagh, M. et al. (1999) *Human Gene Therapy* 10(2):175–187.
Naldini, L. et al., (1996) *Science* 272:263–267.
Quinn, E.R. et al., (1998) *Human Gene Therapy* 9(10):1457–1467.
Uchida, N. et al. (1998) *PNAS USA* 95(20):11939–11944.
Barry, S.C. et al. (2000) "Lentiviral and murine retroviral transduction of T cells for expression of human CD40 ligand" *Human Gene Therapy* 11:323–332.
Chinnasamy D. et al., (2000). "Lentiviral–mediated gene transfer into human lymphocytes: role of HIV–1 accessory proteins" *Blood* 96(4):1309–1316.
Costello, E. et al. (2000) "Gene transfer into stimulated and unstimulated T lymphocytes by HIV–1–dervied lentiviral vectors" *Gene Therapy* 7:596–604.
Douglas, J. et al. (1999) "Efficient transduction of human lymphocytes and CD34+ cells via human immunodeficiency virus–based gene transfer vectos" *Human Gene Therapy* 10:935–945.
Follenzi, A. et al. (2000) "Gene transfer by lentiviral vectors is limited by nuclear translocation and rescued by HIV–1 pol sequences" *Nature Therapy* 25:217–222.
Han, W. et al., (2000) "A soluble form of human Delta–like–1 inhibits differentiation of hematopoietic progenitor cells" *Blood* 95:1616–1625.
Haas, D.L., et al., (2000) "Critical factors influencing stable transduction of human CD34+ cells with HIV–1–derived lentiviral vectors" *molecular Therapy* 2:71–80.
Hooijberg E. et al. (2000) "NFAT–controlled expression of GFP permits visualization and isolation of antigen–stimulated primary human T cells" *Blood* 96:459–466.
Klebba, C. et al. (2000) "Retrovirally expressed anti–HIV ribozymes confer a selective survival advantage on CD4+ T cells in vitro" *Gene Therapy* 7:408–416.
Movasagh, M. et al. (1998) "Successful peripheral T–lymphocyte–directed gene transfer for a patient with severe combined immune deficiency caused by adenosine deaminase deficiency" *Blood* 91:30–36.
St. Croix, B., et al. (2000) "Genes expessed in human tumor endothelium" *Science* 289:1197–1202.
Unutmaz, D. et al. (1999) "Cytokine signals are sufficient for HIV–1 infection of resting human T lymphocytes" *J. Exp. Med.* 11:1735–1746.
Zennou, V., et al., (2000) "HIV–1 genome Nuclear import is mediated by a central DNA flap" *Cell* 101:173–185.

* cited by examiner

Primary Examiner—John L. LeGuyader
Assistant Examiner—Mary Schmidt
(74) Attorney, Agent, or Firm—Morrison & Foerster, LLP

(57) ABSTRACT

The present invention provides methods, as well as compositions related thereto, for the efficient transduction of cells using viral vectors. The efficiency of transduction is increased by contacting the cell to be transduced with one or more molecules that bind the cell surface. Contact with a cell surface binding molecule may occur before, after, or simultaneously with contact between the viral vector and the cell. The transduced vectors may be constructed to express a gene of interest, permitting the transduced cells to be used as therapeutic and prophylactic agents.

30 Claims, 11 Drawing Sheets

Stimulation Day 1

CD4+ EGFP+: 91.22%
MF: 3325

Stimulation Day 0
Transduction Day 1

CD4+ EGFP+: 89.12%
MF: 2962

Stimulation Day 0
Transduction Day 0

CD4+ EGFP+: 80.24%
MF: 1966 pN2CGFP at MOI 20

CD4+ EGFP+: 78.2%
MF: 1966

MOI 2
CD4+ EGFP+: 72.7%
MF: 3438

MOI 5
CD4+ EGFP+: 74.4%
MF: 2410

MOI 10
CD4+ EGFP+: 78.7%
MF: 2628

MOI 15
CD4+ EGFP+: 82.4%
MF: 2822

MOI 20
CD4+ EGFP+: 83.8%
MF: 2780

METHODS FOR STABLE TRANSDUCTION OF CELLS WITH HIV-DERIVED VIRAL VECTORS

TECHNICAL FIELD

The present invention is directed to methods, as well as compositions related thereto, for the efficient and stable transduction of cells using viral vectors. The methods increase the efficiency of transduction by contacting the cell to be transduced with one or more molecules that bind the cell surface. The contacting step may occur before, after, or simultaneously with, introduction of the viral vector to the cells. The present invention also concerns the use of the stably transduced cells in other applications, including expression of nucleic acids borne by the vector or therapy of living organisms.

BACKGROUND ART

"Transfection", which generally refers to techniques for the introduction of genetic material into a cell, has contributed greatly to the molecular and recombinant revolutions in biology. Examples of transfection techniques for use with higher eukaryotic cells include calcium phosphate precipitation, DEAE-dextran treatment, electroporation, microinjection, lipofection, viral infection, and other methods found in numerous scientific textbooks and journals.

Among transfection techniques, the use of viral infection is unique in that a virus naturally occurring means of introducing its genetic material into a cell is taken advantage of to transfer a nucleic acid molecule of interest into a cell. Examples of viruses modified and applied to such techniques include adenoviruses, adeno-associated viruses, herpes simplex viruses, and retroviruses. Generally, nucleic acid molecules of interest may be cloned into a viral genome. Upon replication and packaging of the viral genome, the resultant viral particle is capable of delivering the nucleic acid of interest into a cell via the viral entry mechanism.

Commonly, the viral genome is first made replication deficient by nucleic acid manipulation before the addition of the nucleic acid of interest. The resultant viral genome, or viral vector, requires the use of a helper virus or a packaging system to complete viral particle assembly and release from a cell. When a viral vector or viral particle is used to transfer genetic material of interest into a cell, the technique is referred to as "transduction". Thus generally, to "transduce" a cell is to use a viral vector or viral particle to transfer genetic material into a cell.

Among transduction techniques, the use of retroviruses has been the subject of great interest for the genetic modification of mammalian cells. Of particular interest is the use of modified retroviruses to introduce genetic material into cells to treat genetic defects and other diseases. An example of this approach is seen in the case of cells of the hematopoietic system, where retroviruses and lentiviral vectors are the subject of intense research.

Movassagh et al., for example, discuss their studies on their attempts to increase the efficiency of retrovirus mediated transduction by including results from studies on the cell cycle of activated T cells. As such, their results are dependent upon active cell division during transduction. The work is also limited to the use of a murine onco-retrovirus and the requirement for significant prestimulation of the cells before transduction.

June et al. (WO 96/34970) describe the use of T cell stimulation as a means to increase T cell transfection. Other work on T cell transduction with activated or stimulated cells include those of Douglas et al., Hooijberg et al, Onodera et al., Klebba et al., Barry et al., and Unutmaz et al. Unfortunately, none of this work demonstrated transduction efficiencies of greater than about 65%.

Costello et al. describe the transduction of both stimulated and non-stimulated T cells using Human Immunodeficiency Virus-1 (HIV-1) lentiviral vectors. They observed only about a maximum of 17% efficiency with stimulated primary T cells and less than 19% efficiency with non-stimulated T cells. They also noted a limited ability to increase efficiency to no more than 36% in stimulated T cells by including the presence of HIV-1 accessory proteins.

Chinnasamy et al. also describe an increase in the efficiency of transduction in the presence of HIV-1 accessory proteins in both non-stimulated and mitogen stimulated T cells. Like Movassagh et al, Chinnasamy et al. prestimulated blood lymphocytes for significant periods prior to transduction with a lentiviral vector. While Chinnasamy et al. initially observed a greater than 96% transduction efficiency three days after transduction, the percentage of stably transduced cells decreased to 71.2% two weeks after transduction. Haas et al. also observed transient transduction and "pseudotransduction" in cells transduced with a lentiviral vector capable of expressing a marker gene (green fluorescent protein). Even three days post transduction, significant (over 10%) transient transduction was detected based on non-integrative expression of the marker gene in transduced primary CD34+ cord blood cells. Such expression from transient transduction remained detectable at about 5% even seven days post-transduction. Only after about 10 days post transduction did expression from transient transduction mirror that in cells transduced with a markerless vector.

Therefore, Chinnasamy et al were not able to achieve stable transduction, where an integrated form of the viral vector has been inserted into the chromosomal DNA of the transduced cell, of primary lymphocytes beyond 71.2% as reflected by the efficiency after two weeks. This was despite the use of cytokines to prestimulated the cells. Furthermore, Chinnasamy describe their inability to significantly transduce (only 3.6% 14 days post transduction) non-stimulated lymphocytes with a HIV vector that did not express accessory proteins (Vif, Vpr, Vpu and Nef), even though the cells were later stimulated with the PHA mitogen and the IL-2 cytokine post-transduction. While the results were improved somewhat with the use of non-stimulated cells and vectors containing accessory proteins, in no case was the efficiency of stable transduction of stimulated or non-stimulated cells greater than 75% on day 14 post transduction, irrespective of the stimulatory protocol used with the vector.

Low frequencies of stable transduction with lentiviral vectors was also observed by Hass et al., who could only achieve a maximum stable transduction efficiency of less than 25%, seven days post transduction, with primary CD34 positive cord blood cells. Strikingly, this 25% upper limit of transduction could not be improved even after extremely high multiplicities of infection or vector concentrations, such as a multiplicity of infection (MOI) of up to 9000 and vector concentrations of up to $10^8$ infectious units per milliliter.

Follenzi et al. also used a very high MOI of 500 to transduce cells in the presence of a three cytokine cocktail containing interleukin-3 (IL-3), interleukin-6 (-IL6) and stem cell factor (SCF). Interestingly, use of the cocktail would render the cells unsuitable for human clinical transplantation.

Thus there remains a need to provide a more efficient means of stably transducing cells with vectors at high frequency. Additionally, there is a need for a more efficient means to transduce non-stimulated cells for use both as research tools and as a therapeutic agent.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

The present invention provides highly efficient methods, and compositions related thereto, for the stable transduction of cells with viral vectors and viral particles. By "stable transduction," it is meant where an integrated form of the viral vector has been inserted into the chromosomal DNA of the transduced cell. The methods comprise exposing the cells to be transduced to contact with at least one molecule that binds the cell surface. This contacting step may occur prior to, during, or after the cells are exposed to the viral vector or viral particle. Hereinafter, the term "viral vector" will be used to denote any form of a nucleic acid derived from a virus and used to transfer genetic material into a cell via transduction. The term encompasses viral vector nucleic acids, such as DNA and RNA, encapsidated forms of these nucleic acids, and viral particles in which the viral vector nucleic acids have been packaged.

The present invention also includes the use of the transduced cells in other applications, including production of useful gene products and proteins by expression of a nucleic acid present in the vector or therapy of living subjects afflicted, or at risk of being afflicted with a disease. Preferably, the subject is human.

The at least one molecule that binds the surface of the cells to be transduced includes any molecule that physically interacts with a receptor, marker, or other recognizable moiety on the surface of the cells. In principle, any cell surface binding molecule may be used for high efficiency transduction of cells. Without binding the invention to theory, the cell surface binding molecules may result in the host cell's chromatin being more receptive to DNA integration; in preferential integration of a viral vector into a site favorable for vector gene expression; in more efficient entry of the nucleic acid containing capsid into the cytoplasm; in more efficient entry of the virus across the cell membrane or internal membranous structures such as the endosome; or in making the cell more permissive for nuclear import of the viral vector's genetic material. The methods of the invention may also involve more than one of the above possibilities. Also, and as evident from the number and diversity of the above possibilities, the invention cannot be limited to any one theory. Instead, and given the extraordinary discovery of the invention in the stable transduction of up to 100% of the treated cells without negatively affecting the possible use of the cells in human therapy, the invention should be viewed as opening a new approach in the field of human cell therapy.

Not all cell surface binding molecules, however, will result in the efficient and stable transduction by viral vectors. For example, binding to a cell surface molecule that induces apoptosis will not result in efficient transduction of the cell, but rather cell death. Although cell death may be preferred for the killing of cells (e.g. tumor cells) it is not preferred for the stable transduction of cells with vectors containing payload genes or nucleic acid sequences. A preferred cell surface binding molecule results in the cell being more receptive to transduction by a viral vector. Examples of such molecules include an antibody for a specific cell surface receptor or portion thereof as well as a ligand or binding domain for such a receptor. Moreover, antigen-binding fragments of antibodies, such as $F_{ab}$ and $F_v$ fragments are contemplated for use in the present invention. The binding domain for the specific, cell-surface receptor can contain a single epitope or two or more epitopes.

Preferred examples of cell surface binding molecules for use in the invention are anti-CD3 and anti-CD28 antibodies which bind T cells and make them more receptive to vector transduction. Other preferred cell surface binding molecules are antibodies or ligands for the FLT-3 ligand, TPO, and Kit ligand receptors, which make cells expressing the receptors, such as hematopoietic stem cells, more receptive to vector transduction. Additional preferred cell surface binding molecules are antibodies or ligands for GM-CSF and IL-4 receptors, which make dendritic cells or their precursors, such as monocytes, CD34 positive stem cells, or their differentiated progenitor cells on the dendritic cell lineage, more receptive to vector transduction. Other cell surface binding molecules include molecules found on cell surfaces which bind the surface of another cell.

Additional examples of cell surface binding molecules include polypeptides, nucleic acids, carbohydrates, lipids, and ions, all optionally complexed with other substances. Preferably, the molecules bind factors found on the surfaces of blood cells, such as CD1a, CD1b, CD1c, CD1d, CD2, CD3γ, CD3δ, CD3∈, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79α, CD79β, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD114, CD115, CD116, CD117, CD118, CD119, CD120a, CD120b, CD121a, CD121b, CD122, CD123, CDw124, CD125, CD126, CDw127, CDw128a, CDw128b, CDw130, CDw131, CD132, CD133, CD134, CD135, CD136, CDw137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCRζ. Small letters (e.g. "a" or "b") indicate complex CD molecules composed of multiple gene products or belonging to families of structurally related proteins. The notation "w" refers to putative CD molecules that have not yet been fully confirmed. A more complete listing of CD molecules is found in Kishimoto, T. (ed). Current information on CD molecules is also found in Shaw, S. (ed)., Protein Reviews on the Web: An International WWW Resource/Journal at http://www.bsi.vt.edu/immunology.

More preferred are molecules that bind factors found on the surfaces of lymphocytes, T cells and leukocytes, such as CD2, CD3γ, CD3δ, CD3∈, CD5, CD6, CD7, CD8α, CD8β, CD9, CD11a, CD18, CD25, CD26, CD27, CD28, CD29, CD30, CD37, CD38, CD39, CD43, CD44, CD45R, CD46, CD48, CD49a, CD49b, CD49c, CD49d, CD49e, CD49f, CD50, CD53, CD54, CD56, CD57, CD58, CD59, CDw60, CD62L, CD68, CD69, CDw70, CD71, CD73, CDw75, CDw76, CD84, CD85, CD86, CD87, CD89, CD90, CD94, CD96, CD97, CD98, CD99, CD100, CD101, CD103, CD107a, CD107b, CDw108, CDw109, CD118, CD119, CD120b, CD121a, CD122, CDw124, CDw127, CDw128a, CDw130, CD132, CD134, CDw137, CD140a, CD140b, CD143, CD146, CD148, CD152, CD153, CD154, CD155, CD161, CD162, CD165, CD166, and TCRζ.

Additional antibodies and molecules that bind to the surface of cells, and suitable for use in the present invention, are disclosed in Linscott's Directory of Immunological and Biological Reagents, 11th Edition, January 2000, Publisher: W.D. Linscott, Petaluma, Calif., which is hereby incorporated by reference as if fully set forth. In some embodiments of the invention, however, the cell surface binding molecule is not a cytokine.

While the invention may be practiced by use of soluble cell surface binding molecules that promote vector transduction of cells, other preferred embodiments include the use of immobilized cell surface binding molecules. Preferably, the immobilized molecules are antibodies. Alternatively, immobilization may be via use of other cells that express the cell surface binding molecules. A preferred method for the efficient transduction of hematopoietic stem cells is to include bone marrow stromal cells, expressing ligands on their surface that facilitate stem cell maintenance without differentiation, during transduction. The stimulating cells are not restricted to native cells, but any cell can be engineered to express the appropriate cell surface binding molecule in order to provide the correct stimulus for transduction.

Additional molecules that increase or reinforce the ability of the at least one molecule to bind the cell surface may also be included. For example, a soluble form of a (primary) antibody for a specific cell surface receptor may be used in combination with a secondary antibody that can crosslink primary antibodies already bound to the cell surface.

Of course any cell can be used in the practice of the invention. Preferably, the cell to be transduced is a eukaryotic cell. More preferably, the cell is a primary cell. Cell lines, however, may also be transduced with the methods of the invention and, in many cases, more easily transduced. In one preferred embodiment, the cell to be transduced is a primary lymphocyte (such as a T lymphocyte) or a macrophage (such as a monocytic macrophage), or is a precursor to either of these cells, such as a hematopoietic stem cell. Other preferred cells for transduction in general are cells of the hematopoietic system, or, more generally, cells formed by hematopoiesis as well as the stem cells from which they form and cells associated with blood cell function. Such cells include granulocytes and lymphocytes formed by hematopoiesis as well as the progenitor pluripotent, lymphoid, and myeloid stem cells. Cells associated with blood cell function include cells that aid in the functioning of immune system cells, such as antigen presenting cells like dendritic cells, endothelial cells, moncytes, and Langerhans cells. In a preferred embodiment, the cells are T lymphocytes (or T cells), such as those expressing CD4 and CD8 markers.

In particularly preferred embodiments, the cell is a primary CD4+ T lymphocyte or a primary CD34+ hematopoietic stem cell. However, and given that the viral vectors for use in the invention may be pseudotyped with Vesicular Stomatitis Virus envelope G protein (as discussed below), any cell can be transduced via the methods of the present invention. Such a cell includes, but is not limited to, an astrocyte, a skin fibroblast, a epithelial cell, a neuron, a dendritic cell, a lymphocyte, a cell associated with the immune response, a vascular endothelial cell, a tumor cell, a tumor vascular endothelial cell, a liver cell, a lung cell, a bone marrow cell, an antigen presenting cell, a stromal cell, an adipocyte, a muscle cell, a pancreatic cell, a kidney cell, an ovum or spermatocyte (e.g. to create transgenic animals), a cell that contributes to the germ line, a embryonic pluripotential stem cell or its progenitors, a blood cell including non-nucleated cells such as platelets and erythrocytes, and the like. Preferably, the cell is of a eukaryotic, multicellular species (e.g., as opposed to a unicellular yeast cell), and, even more preferably, is of mammalian origin, e.g., a human cell.

A cell to be transduced can be present as a single entity, or can be part of a larger collection of cells. Such a "larger collection of cells" can comprise, for instance, a cell culture (either mixed or pure), a tissue (e.g., epithelial, stromal or other tissue), an organ (e.g., heart, lung, liver, gallbladder, urinary bladder, eye, and other organs), an organ system (e.g., circulatory system, respiratory system, gastrointestinal system, urinary system, nervous system, integumentary system or other organ system), a blastocyst, a embryonic stem cell a cell from a fetus (e.g. for the treatment of a genetic disorder/disease or for creating transgenic animals), diseased tissues such as a tumor or the site of an infection, or an organism (e.g., a bird, mammal, marine organism, fish, plant or the like). Preferably, the organs/tissues/cells being targeted are of the circulatory system (including for example, but not limited to heart, blood vessels, and blood), respiratory system (e.g., nose, pharynx, larynx, trachea, bronchi, bronchioles, lungs, and the like), gastrointestinal system (including for example mouth and oral tissues, pharynx, esophagus, stomach, intestines, salivary glands, pancreas, liver, gallbladder, and the like), mammary system (such as breast epithelial cells and supporting cells in the tissue), urinary system (such as kidneys, ureters, urinary bladder, urethra, and the like), nervous system (including, but not limited to, brain and spinal cord, and special sense organs, such as the eye) and integumentary system (e.g., skin).

Even more preferably, the cells to be transduced are selected from the group consisting of heart, blood vessel, including tumor blood vessels and blood vessels associated with infected or diseased tissue, bone marrow, blood, brain, lymphatic tissue, lymph node, spleen, lung, liver, gallbladder, urinary bladder, and eye cells. In one particular embodiment of the invention, the cell is autologous to the intended host for use, but cells allogenic, partially mismatched, completely mismatched, or even xenogenic to the host may also be used. Furthermore, universal donor cells, suitable for use in any given host organism, a related group of organisms or a species, such as human beings, may be transduced. This latter embodiment of the invention is particularly important in the transplantation of cells, tissues or organs, where the source of the transduced cells may be critical to the outcome of the transplant.

Another preferred cell for transduction by the methods of the invention is a tumor cell, a diseased cell, or a cell at risk for becoming abnormal over time due to its genetic makeup or the genetic makeup of other cells present in the same organism. The latter embodiment permits the transduced cells of the invention to be used in prophylaxis. Breast cancer is one example of a disease process where prognostic indicators would allow for treatment with the transduced cells of the invention as early genetic intervention before the disease ensues. However, the methods of the invention may also be used in the therapeutic treatment of breast cancer after the disease has been detected. Additional applications of the invention in cancer therapy are numerous, and one skilled in the art would be able to use the invention set out herein for the treatment of many types of cancers without undue experimentation.

By way of example, and without limiting the present invention, one application is in breast cancers that are estrogen dependent. The cancer cells in estrogen-dependent breast cancer would be preferentially transduced by using antibodies or ligands that bind the estrogen receptor in combination with a therapeutic viral vector. The vector may contain, for example, a tumor inhibiting gene, such as the Herpes virus thymidine kinase gene. The transduced cells can thus be selectively killed by the addition of gancyclovir, a pro-drug that can be activated by Herpes thymidine kinase. Additional examples of tumor inhibiting genes and a corresponding pro-drug are numerous and well known in the art and may be selected by the skilled artisan without undue experimentation. The use of activatable pro-drugs in combination with application of the transduction methods of the invention may be broadly applied to other tumor types, and the above example does not limit the invention to tumors that are hormonal dependent or dependent upon some soluble factor for growth or proliferation.

For example, Her-2/neu positive tumor cells are not estrogen dependent, and a poor prognostic indicator since non-estrogen dependent tumors containing such cells are highly resistant to treatment with drugs such as taxol, an estrogen antagonist. A preferred embodiment to the invention is to include antibodies or other molecules that bind Her-2/neu or heregulin with viral vector preparations during transduction of tumor contaminated cells, such as in a bone marrow transplantation protocol. Alternatively, the transduction may be made directly to the tumor site, or intra vascularly in vivo with vectors that would modulate tumorigenesis.

Yet another embodiment of the invention is to target the tumor vasculature, alone or in combination with targeting the tumor cells. St Croix et al., which is hereby incorporated by reference as if fully set forth, have identified genes that are specifically overexpressed in tumor endothelial cells as compared to normal endothelium by SAGE analysis. Many of these genes encode cell surface molecules, such as the Thy-1 cell surface antigen or Endo180 lectin. All of the upregulated cell surface factors may be bound by a cell surface binding molecule of the invention to provide a stimulus for efficient stable gene transduction. Thus, an approach for tumor therapy would be to destroy the tumor vasculature by killing tumor endothelial cells after transducing them with a therapeutic viral vector in the presence of cell surface binding molecules that bind selectively to tumor vasculature and not normal endothelial cells.

In yet another embodiment of the invention is selective expression of an anti-tumor gene in tumor vasculature by incorporating elements (e.g. promoters or cis-acting stabilizing/degradation elements on mRNA) in the viral vector that selectively promote expression of the anti-tumor gene in tumor but not in normal vascular endothelium. Such methods can occur ex vivo, in vitro or in vivo. In vivo is the preferred method for therapy if the tumor vascular endothelium is targeted. Alternatively, and if the goal is to purge bone marrow of contaminating tumor cells for bone marrow transplantation, for example, then the preferred method for therapy occurs ex vivo or in vitro.

Furthermore, in vivo uses are not restricted to disease states and can be used to transduce normal cells. For example, the invention may be used to transduce hematopoietic stem cells in vivo in the bone marrow. Any combination of antibodies or other cell surface binding molecules, such as FLT-3 ligand, TPO and Kit ligand, or functional analogs thereof, or stromal cells expressing the cell surface binding molecule, could be added with vector upon direct injection into the bone marrow for high efficiency bone marrow transduction. The term "functional analog" refers to any molecule that retains the cell surface binding activity of a cell surface binding molecule of the invention. Such functional analogs include fragments of FLT-3 ligand, TPO and Kit ligand; FLT-3 ligand, TPO and Kit ligand molecules containing one or more amino acid substitutions, additions or deletions; and antibodies that mimic the cell surface binding activity of a cell surface binding molecule.

An alternative approach to the above is to use bone marrow stromal cells as producer cells for the viral vector and thus provide the vector and cell surface binding molecule via cell therapy and not as a vector preparation. Another example is the transduction of T cells or dendritic cells by adding functional analogs of CD3 and CD28 antibodies or GM-CSF and IL-4, respectively, with vector during subcutaneous injection. The lymph in the subcutaneous tissue would drain the vector and stimulants into the lymph nodes for efficient transduction of the targeted cells.

The present invention includes the advantage that optionally, purification of the cell to be transduced is not essential. Transduction of mainly a cell type of interest can be accomplished by the choice of cell surface moiety to be bound. Thus in a mixed population of blood cells, for example, transduction of cells expressing CD3, such as certain T cells, will be enhanced when CD3 specific antibodies are used to interact with the cells. This will occur in preference over other cell types in the population, such as granulocytes and monocytes that do not express CD3.

The invention also encompasses the transduction of purified or isolated cell types if desired. The use of a purified or isolated cell type provides additional advantages such as higher efficiencies of transduction due to higher vector concentrations relative to the cell to be transduced.

When purified T cells are to be transduced, the at least one molecule preferably binds a cell surface molecule found on T cells. Examples of such cell surface molecules include CD3, CD28, CD25, CD71, and CD69. Examples of molecules that bind to these cell surface molecules include antibodies and monoclonal antibodies that recognize them, many of which are commercially available or readily and routinely prepared using standard techniques without undue experimentation. In a preferred embodiment for the transduction of CD4+ or CD8+ cells, monoclonal antibodies that recognize CD3 and/or CD28 may be used. Commercially available examples of such antibodies include OKT3 for CD3 and CD28.2 for CD28. These antibody molecules may be used in a soluble form, optionally later crosslinked by other molecules, or in an immobilized form such as on beads or other solid surfaces. In a particularly preferred embodiment of the invention, the antibodies are immobilized on the surface of the vessel, such as the walls of a tissue culture well, plate, or bag used for the viral vector mediated transduction. Without being bound by theory, use of immobilized antibodies on the surface where cells adhere or make contact may increase local concentrations of cell surface interactions on the cell surface.

When hematopoietic stem cells are to be transduced, antibodies specific for the hematopoietic stem cell receptor of the FLT-3 ligand, TPO (Thrombopoietin or Megakaryocyte Growth and Development Factor), or Kit ligand may be used as the cell surface binding molecule. Alternatively, antibodies to stem cell positive cell markers, including, but not limited to CD34 or AC 133, may be used. When a ligand containing compound or composition is used as a cell surface binding molecule, the whole native ligand-containing proteins, ligands or ligands bound to heterologous proteins can be used either in a soluble or immobilized form. Immobilized forms include attachment to microbeads, directly or indirectly, using, for example, avidinibiotin.

Alternatively, the ligand may be expressed in the viral envelope of the viral vector, optionally in the form of a chimeric or fusion proteins, and/or complexed (covalently or non-covalently) with one or more other protein(s). In such embodiments, the cell surface binding molecule is presented in combination with the viral vector as a single composition for transducing cells. Additional examples of cell surface binding molecules that may be expressed in viral envelopes include the numerous surface factors listed above.

Other preferred cell surface binding molecules, such as antibodies or fragments thereof, are those that bind to the hematopoietic stem cell receptors of Notch or Delta, or the Notch or Delta proteins themselves, or the ligands of Notch or Delta that are bound to heterologous proteins. Delta and Notch encode cell surface proteins that influence a wide variety of cell fate decisions in Drosophila development. Vertebrate homologues of Delta and Notch are essential for normal embryonic development. Delta homologues are importantly involved in the regulation of hematopoiesis. Delta-Serrate-lag2 (DSL), a soluble form of a homologue, enhances expansion of primitive hematopoietic precursors. When combined with hematopoietic growth factors, including interleukin-3 (IL-3), granulocyte colony-stimulating fact or (G-CSF) or granulocyte-macrophage colon-stimulating factor (GM-CSF), DSL promotes the expansion of primitive hematopoietic progenitors and at the same time inhibited the differentiation of primitive precursors into more mature precursor cells responsive to IL-3 alone (see Han et al.). DSL most likely acts by activating the Notch receptor expressed in hematopoietic cells, modulating cellular competence to respond to conventional hematopoietic growth factors by selectively blocking cell differentiation, but not proliferation signals (see Han and Moore, Blood 1999). Therefore, Delta and Notch homologues, antibodies that are functional analogs to the homologues, are further preferred cell surface binding molecules for use in achieving greater than 75% efficient vector transduction of cells, particularly hematopoietic stem cells.

The present invention includes viral vectors, and compositions comprising them, for use in the disclosed methods. The vectors are preferably retroviral (family Retroviridae) vectors, and more preferably lentiviral vectors. Other retroviral vectors, such as oncoviral and murine retroviral vectors, may also be used. Additional vectors may be derived from other DNA viruses or viruses that can convert their genomes into DNA during some point of their life cycle. Preferably the viruses are from the families Adenoviridae, Parvoviridae Hepandaviridae (including the hepatitis delta virus and the hepatitis E virus which is not normally classified in the Hepandaviridae), Papoviridae (including the polyomavirinae and the papillomavirinae), Herpesviridae, and Poxviridae.

Additional viruses of the family Retroviridae (i.e., a retrovirus), are of the genus or subfamily Oncovirinae, Spumavirinae, Spumavirus, Lentivirinae, and Lentivirus. An RNA virus of the subfamily Oncovirinae is desirably a human T-lymphotropic virus type 1 or 2 (i.e., HTLV-1 or HTLV-2) or bovine leukemia virus (BLV), an avian leukosissarcoma virus (e.g., Rous sarcoma virus (RSV), avian myeloblastosis virus (AMV), avian erythroblastosis virus (AEV), and Rous-associated virus (RAV; RAV-0 to RAV-50), a mammalian C-type virus (e.g., Moloney murine leukemia virus (MuLV), Harvey murine sarcoma virus (HaMSV), Abelson murine leukemia virus (A-MuLV), AKR-MuLV, feline leukemia virus (FeLV), simian sarcoma virus, reticuloendotheliosis virus (REV), spleen necrosis virus (SNV)), a B-type virus (e.g., mouse mammary tumor virus (MMTV)), and a D-type virus (e.g., Mason-Pfizer monkey virus (MPMV) and "SAIDS" viruses).

An RNA virus of the subfamily Lentivirus is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. The acronym "HIV" or terms "AIDS virus" or "human Immunodeficiency virus" are used herein to refer to these HIV viruses, and HIV-related and -associated viruses, generically. Moreover, a RNA virus of the subfamily Lentivirus preferably is a Visna/maedi virus (e.g., such as infect sheep), a feline immunodeficiency virus (FIV), bovine lentivirus, simian immunodeficiency virus (SIV), an equine infectious anemia virus (EIAV), and a caprine arthritis-encephalitis virus (CAEV).

A particularly preferred lentiviral vector is one derived from HIV, most preferably HI-1, HIV-2, or chimeric combinations thereof. Of course different serotypes of retroviruses, especially HIV, may be used singly or in any combination to prepare vectors for use in the present invention. Preferred vectors of the invention contains cis acting elements that are present in the wild-type virus, but not present in a "basic" lentiviral vector. A "basic" lentiviral vector contains minimally, LTRs and packaging sequences in the 5' leader and gag encoding sequences, but can also optionally contain the RRE element to facilitate nuclear export of vector RNA in a Rev dependent manner. A preferred vector additionally contains nucleotide sequences that enhance the efficiency of transduction into cells.

An example of such a vector is pN2cGFP, a vector that contains the complete sequences of gag and pol. Another example is a vector that contain sequences from about position 4551 to position 5096 in pol (reference positions from the pNL4-3 sequence, Accession number M19921, HIVNL43 9709 bp, kindly provided by C. E. Buckler, NIAID, NIH, Bethesda, Md.). However any cis-acting sequence from the wt-HIV that can improve vector transduction efficiency may be used. Other examples of vectors capable of efficient transduction via the present invention are cr2HIV constructs as described in U.S. Pat. No. 5,885,806.

A previously identified sequence that is insufficient to significantly increase transduction efficiency described by Zennou et al. (2000) as a central DNA flap (a 178 base pair fragment from positions 4793 to 4971 on pLAI3, corresponding to positions 757 to 4935 on pNL4-3) capable of increasing transduction efficiency. The present invention includes the discovery that while this small fragment is not sufficient to increase the transduction efficiency, a larger 545 base pair fragment (positions 4551 to 5096 in pNL4-3), or yet larger fragments containing it, was capable of increasing transduction as part of the present invention.

Additional examples of viral vector constructs that may be used in the present invention are found in U.S. Pat. No. 5,885,806, which is hereby incorporated by reference as if fully set forth. The constructs in U.S. Pat. No. 5, 885,806 are merely examples that do not limit the scope of vectors that efficiently transduce cells. Instead, the constructs provide additional guidance to the skilled artisan that a viral vector for use with the present invention may contain minimal sequences from the wild-type virus or contain sequences up to almost the entire genome of wild-type virus, yet exclude an essential nucleic acid sequence required for replication and/or production of disease. Methods for determining precisely the sequences required for efficient transduction of cells are routine and well known in the art. For example, a systematic incorporation of viral sequences back into a "basic" vector or deleting sequences from vectors that contain virtually the entire HIV genome, such as cr2HIVs, is routine and well known in the art.

Furthermore, placing sequences from other viral backbones into viral vectors of interest, such as the cytomegalovirus (CMV), is also well known in the art. Regardless of the actual viral vector used, various accessory proteins encoded by, and sequences present in, the viral genetic material may be left in the vector or helper genomes if these proteins or sequences increase transduction efficiency in certain cell types. Numerous routine screens are available to determine whether certain genetic material increases transduction efficiency by incorporating the sequence in either the vector or helper genomes. A preferred embodiment of the invention is to not include accessory proteins in either the vector or helper genomes. But this preference does not exclude embodiments of the invention where accessory proteins and other sequences are left in either the vector or a helper genome to increase transduction efficiency.

The viral vectors used in the present invention may also result from "pseudotype" formation, where co-infection of a cell by different viruses produces progeny virions containing the genome of one virus encapsulated within an outer layer containing one or more envelope protein of another virus. This phenomenon has been used to package viral vectors of interest in a "pseudotyped" virion by co-transfecting or co-infecting a packaging cell with both the viral vector of interest and genetic material encoding at least one envelope protein of another virus or a cell surface molecule. See U.S. Pat. No. 5,512,421. Such mixed viruses can be neutralized by anti-sera against the one or more heterologous envelope proteins used. One virus commonly used in pseudotype formation is the vesicular stomatitis virus (VSV), which is a rhabdovirus. The use of pseudotyping broadens the host cell range of the virus by including elements of the viral entry mechanism of the heterologous virus used.

Pseudotyping of viral vectors and VSV for use in the present invention results in viral particles containing the viral vector nucleic acid encapsulated in a nucleocapsid which is surrounded by a membrane containing the VSV G protein. The nucleocapsid preferably contains proteins normally associated with the viral vector. The surrounding VSV G protein containing membrane forms part of the viral particle upon its egress from the cell used to package the viral vector. Examples of packaging cells are described in U.S. Pat. No. 5,739,018. In a preferred embodiment of the invention, the viral particle is derived from HIV and pseudotyped with VSV G protein. Pseudotyped viral particles containing the VSV G protein can infect a diverse array of cell types with higher efficiency than amphotropic viral vectors. The range of host cells include both mammalian and non-mammalian species, such as humans, rodents, fish, amphibians and insects.

The viral vector for use in the transduction methods of the invention can also comprise and express one or more nucleic acid sequences under the control of a promoter present in the virus or under the control of a heterologous promoter introduced into the vector. The promoters may further contain insulatory elements, such as erythroid DNAse hypersensitive sites, so as to flank the operon for tightly controlled gene expression. Preferred promoters include the HIV-LTR, CMV promoter, PGK, U1, EBER transcriptional units from Epstein Barr Virus, tRNA, U6 and U7. While Pol II promoters are preferred, Pol III promoters may also be used. Tissue specific promoters are also preferred embodiments. For example, the beta globin Locus Control Region enhancer and the alpha & beta globin promoters can provide tissue specific expression in erythrocytes and erythroid cells. Another further preferred embodiment is to use cis-acting sequences that are associated with the promoters. For example, The U1 gene may be used to enhance antisense gene expression where non-promoter sequences are used to target the antisense or ribozymes molecule to a target spliced RNA as set out in U.S. Pat. No. 5,814,500, which is hereby incorporated by reference.

Of course any cis acting nucleotide sequences from a virus may be incorporated into the viral vectors of the invention. In particular, cis acting sequences found in retroviral genomes are preferred. For example, cis-acting nucleotide sequence derived from the gag, pol, env, vif, vpr, vpu, tat or rev genes may be incorporated into the viral vectors of the invention to further increase tranduction efficiency. Preferably, a cis acting sequence does not encode an expressed polypeptide; is not expressed as a polypeptide or part thereof due to genetic alteration, such as deletion of a translational start site; encodes only a portion or fragment of a larger polypeptide; or is a mutant sequence containing one or more substitutions, additions, or deletions from the native sequence. An example of a cis acting sequence is the cPPT (central polypurine tract) sequence identified within the HIV pol gene.

Said one or more nucleic acid sequences in the viral vectors of the invention may be found in the virus from which the vector is derived or be a heterologous sequence. The sequence is preferably a full-length or partial sequence that is or encodes a gene product of interest. Such sequences and gene products are preferably biologically active agents capable of producing a biological effect in a cell. Examples of such agents include proteins, ribonucleic acids, enzymes, transporters or other biologically active molecules.

In one preferred embodiment, the agent is a protein, such as a toxin, transcription factor, growth factor or cytokine, structural protein, or a cell surface molecule. The protein may contain one or more domains for which no function has been identified and may be homologous to the transduced cell. Additionally, the protein may be absent, deficient or altered in the cell to be transduced. Alternatively, the protein may be a transdominant negative mutant or a decoy to prevent a natural protein from carrying out its normal activity in the transduced cell.

For example, the nucleic acid sequence may code for a ribozyme that binds, cleaves and destroys RNA expressed, or to be expressed, in the transduced cell. Alternatively, the nucleic acid sequence may code for an antisense molecule designed to target a particular nucleic acid sequence and result in its degradation. The vector contained sequence may be overexpressed, inducibly expressed, or under cellular or viral regulatory transcription control in the transduced cell. Depending on the intended use, the heterologous sequence may encode any desired protein including a marker for transduced cells. Such markers include selectable markers such as a particular resistance phenotype, such as neomycin, MDR-1 (P-glycoprotein), $O^6$-methylguanine-DNA-methyltransferase (MGMT), dihydrofolate reductase (DHFR), aldehyde dehydrogenase (ALDH), glutathione-S-transferase (GST), superoxide dismutase (SOD) and cytosine deaminase. See Koc et al., which is hereby incorporated by reference, for a review.

In the methods of the invention, the cells to be transduced are exposed to contact with the at least one molecule that binds the cell surface before, after, or simultaneously with application of the viral vector. For example, the cells can be cultured in media with CD3 and CD28 antibodies (coated onto the surface of the culture dish or immobilized on beads present in the culture) before, after, or in the presence of the viral vector to be transduced. Preferably, the cells are exposed to immobilized CD3 and/or CD28 only after or only upon initial contact with the viral vector. Under these conditions, the cells are not exposed to cell surface binding molecule(s) prior to actual transduction with the viral vector. In embodiments where contact with a cell surface binding molecule occurs after exposure of the cells to a viral vector (transduction), the contact preferably occurs within three days of transduction, more preferably within one to two days after transduction.

Incubation of the cells with the viral vector may be for different lengths of time, depending on the conditions and materials used. Factors that influence the incubation time include the cell, vector and MOI (multiplicity of infection) used, the molecule(s) and amounts used to bind the cell surface, whether and how said molecule(s) are immobilized or solubilized, and the level of transduction efficiency desired. Preferably, the incubation is for about eight to about 72 hours, more preferably for about 12 to about 48 hours. In a particularly preferred embodiment, the incubation is for about 24 hours and is optionally repeated once.

Contact between the cells to be transduced and a viral vector occurs at least once, but it may occur more than once, depending upon the cell type. For example, high efficiency transduction of CD34 positive stem cells have been accomplished with multiple transductions with vector. A preferred method of the invention is to simultaneously introduce a viral vector in combination with a cell surface binding molecule (e.g. CD3 and/or CD28 antibodies or a FLT-3 ligand, TPO or Kit ligand) and avoid changing the medium for between about one and about eight days after transduction. More preferably, the medium is not changed for three days post transduction. Transduction can proceed for as long as the conditions permit without the process being significantly detrimental to the cells or the organism containing them. Additional examples of cell surface binding proteins for such use include those described hereinabove.

Similarly, the MOI used is from about 1 to about 400, preferably less than 500. Generally, the preferred MOI is from about 2 to about 50. More preferably, the MOI is from about 10 to about 30, although ranges of from about 1 to about 10, about 20, about 30, or about 40 are also contemplated. Most preferred is an MOI of about 20. Furthermore, the copy number of viral vector per cell should be at least one. However, many copies of the vector per cell may also be used with the above described methods. The preferred range of copies per cell is from about 1 to about 100. The more preferred copy number is the minimum copy number that provides a therapeutic, prophylactic or biological impact resulting from vector transduction or the most efficient transduction.

For therapeutic or prophylactic applications, a more preferred copy number is the maximum copy number that is tolerated by the cell without being significantly detrimental to the cell or the organism containing it. Both the minimum and maximum copy number per cell will vary depending upon the cell to be transduced as well as other cells that may be present. The optimum copy number is readily determined by those skilled in the art using routine methods. For example, cells are transduced at increasing increments of concentration or multiplicities of infection. The cells are then analyzed for copy number, therapeutic or biological impact and for detrimental effects on the transduced cells or a host containing them (e.g. safety and toxicity).

After incubation with the viral vector in vitro, the cells may be cultured in the presence of the cell surface binding molecule(s) for various times before the cells are analyzed for the efficiency of transduction or otherwise used. Alternatively, the cells may be cultured under any conditions that result in cell growth and proliferation, such as incubation with interleukin-2 (IL-2) or incubation with the cell surface binding molecule(s) followed by IL-2. Post transduction incubation may be for any period of time, but is preferably from about one to about seven to ten days. Longer periods of time, such as about 14 days, may also be used, although periods that are detrimental to cell growth are not preferred. In embodiments of the invention where the cells are cultured with the cell surface binding molecule(s) before incubation with the viral vector, the culture times may range from about 24 to about 72 hours, most preferably 24 hours.

Such pre-transduction culturing may be compared to stimulation of cells, with cytokines and/or mitogens for example, prior to transduction as taught in the art. The present invention includes advantages resulting from the avoidance of such stimulation. For example, stimulation expands the numbers of cells through proliferation to result in many more cells post-stimulation than pre-stimulation. Transduction of this expanded set of cells requires much more viral vector and related transduction materials (e.g. containers, media, cytokines etc), increasing the associated cost. Furthermore, the stimulation of cells affects their quality for further applications. Movassagh et al. describe the use of a three day pre-transduction stimulation that resulted in deterioration of the T cell repertoire diversity after transduction and further culturing. Additionally, pre-transduction stimulation removes the advantage available from the transduction of cells that are not actively dividing.

The efficiency of transduction observed with the present invention is from about 75–100%. Preferably, the efficiency is at least about 75 to 90%. More preferred embodiments of the invention are where transduction efficiency is at least about 90 to 100%. Most preferred embodiments have transduction efficiencies of at least 91, 92, 93, 94, 95, 96, 97, 98, 99 and 100%.

In addition to the above, the transduced cells may be used in research or for treatment or prevention of disease conditions in living subjects. An example of a research use is the structure-function studies described by Unutmaz et al. Therapeutic uses for the transduced cells include the introduction of the cells into a living organism. For example, unstimulated primary T cells isolated from an individual infected with, or at risk of being infected with HIV, may be first transduced by a vector, like that described in U.S. Pat. No. 5,885,806, using the present methods and followed by injection of the transduced cells back into the individual. Alternatively, the cells may be used directly for the expression of a heterologous sequence present in the viral vector.

When used as a part of HIV therapy or prophylaxis, the vector may encode a toxin or other anti-viral agent that has been adapted for anti-HIV applications. Alternatively, the vector may encode an agent designed to target HIV, such as transdominant negative mutants of the tat, rev, nef, vpu, or vpr genes. In other applications the transduced cell may be corrected to express an appropriate globin gene to correct sickle cell anemia or thalassaemia. Immune cells may also be transduced to modulate their immune function, their response to antigen, or their interactions with other cells. The skilled artisan is aware of the above uses for the present transduction methods as well as numerous other uses and applications known in the art.

BRIEF DESCRIPTION OF THE FIGURES

FIGS. 4A and 4B show the results of FACS analysis for CD4+ and GFP+ cells at 14 days post transduction using either IL-2 and PHA-P or bead immobilized CD3 and CD28 antibodies. Approximately 93% of the antibody treated cells remained stably transduced after 14 days. Only about 75% of cells treated with IL-2 and PHA remained stably transduced after that time.

MODES OF CARRYING OUT THE INVENTION

Figure 1A:
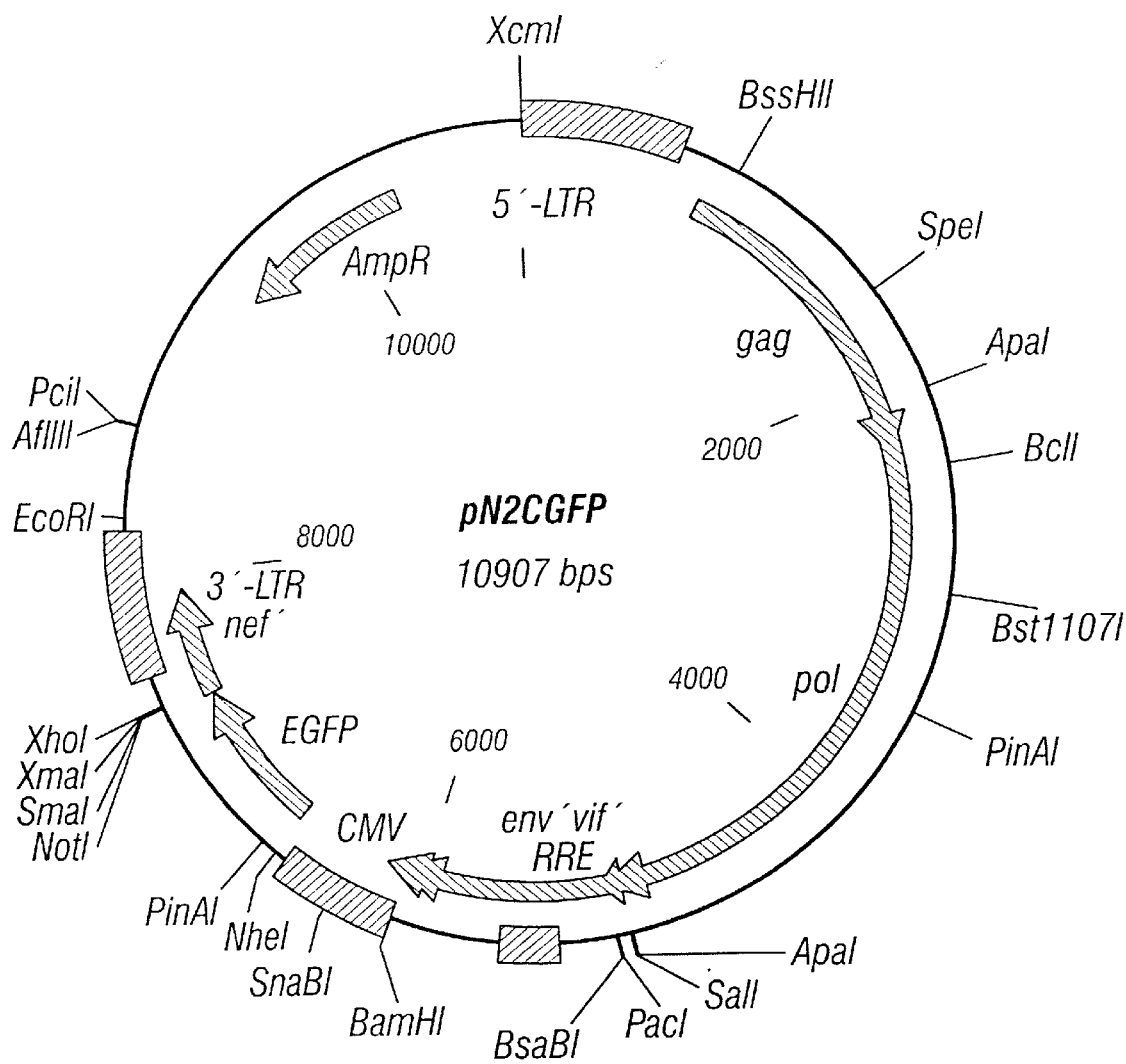
FIGS. 1A and 1B show maps of pN2cGFP and pN1GFP (cPT), respectively. Various restriction enzyme sites are indicated as well as the components derived from HIV. The pN2cGFP construct contains the GFP coding sequence operably linked to a CMV (cytomegalovirus) promoter, thus controlling GFP expression. The pN1GFP(cPT) construct is also referred to as pN1(cpt)CGFP below and contains the cPPT from the HIV pol gene. These constructs are used in the examples described below.

The present invention is directed to methods, and compositions related thereto, for the stable transduction of cells with viral vectors to efficiencies of greater than about 75%. Stably transduced cells may be distinguished from transiently transduced, or pseudotransduced cells, after about seven to ten days, or optionally after about 14 days, post transduction. The methods relate to the fact that contact of the cells to be transduced with at least one molecule that binds the cell surface increases the efficiency of stable transduction. Surprisingly, the contacting step may occur after the transduction step. Even more surprisingly, the highest levels of stable transduction were seen when transduction occurred first followed by contact with immobilized cell surface binding molecules.

The methods of the invention comprise the step of transduction with a viral vector in combination with contact with a cell surface binding molecule. As noted above, the contact may occur before, after or at the same time as transduction with the vector. The invention is broadly applicable to any cell, and the use of any cell surface binding molecule. Cells for use with the present methods include unstimulated primary cells, which are freshly isolated from an in vivo source as well as cell lines, which may have been previously cultured for various times in the presence of factors which maintain them in a proliferating state. When cell lines are used, they may be first cultured in the absence of stimulatory factors prior to transduction with the present methods.

In the case of primary cells, they are first obtained from an in vivo source followed optionally by selection for particular cell types. For example, if primary CD4+ and/or CD8+ T cells are to be used, peripheral blood (PB) or cord blood ("CB" from an umbilical source) samples are first obtained followed by enrichment for CD4+ and/or CD8+ cell types. Standard magnetic beads positive selection, plastic adherence negative selection, and/or other art recognized standard techniques may be used to isolate CD4+ and/or CD8+ cells away from contaminating PB cells. Purity of the isolated cell types may be determined by immunophenotyping and flow cytometry using standard techniques.

After isolation, the primary cells may be used in the present methods to be transduced with viral vectors at efficiencies of greater than 75%. The invention is most advantageously used with primary lymphocytes, such as T cells, transduced with an HIV-1 based vector capable of expressing heterologous genetic material of interest. Another preferred use is with primary hematopoietic stem cells, such as CD34 positive cells. In cases where the heterologous genetic material is or encodes a therapeutic or prophylactic product for use in vivo to treat or prevent a disease, the transduced primary cell can be introduced back into an in vivo environment, such as a patient. As such, the invention contemplates the use of the transfected cells in gene therapy to treat, or prevent, a disease by combating a genetic defect or targeting a viral infection.

The invention is also contemplated for use in efficiently transducing cells for determining the function of a gene, expressing genes efficiently in mammalian cells, expressing genetic libraries (cDNA libraries and genetic antisense or ribozymes libraries) for functional screening for genes of interest, use in protein-protein or protein-nucleic acid two-hybrid like detection strategies, gene trapping approaches, high-throughput gene screening analysis with a microarray or protein array, or studies employing SAGE, proteomics and other functional analytical methods.

For the transduction of primary cells in a mixed population, the above isolation/purification steps would not be used. Instead, the cell to be transduced would be targeted by selection of at least one appropriate cell surface molecule or moiety found on that cell type and the preparation of one or more molecules capable of binding said moiety. The cell surface moiety may be a receptor, marker, or other recognizable epitope on the surface of the targeted cells. Once selected, molecules that interact with the moiety, such as specific antibodies, may be prepared for use in the present invention.

For example, CD4+ and/or CD8+ cells can either be first purified and then transduced by the methods of the invention with the use of immobilized CD3 and CD28 antibodies or alternatively be transduced as part of a mixed population, like peripheral blood cells (PBCs) or peripheral blood mononuclear cells (PBMNCs), by use of the same antibodies. Hematopoietic stem cells in total white blood cell populations, which may be difficult to purify or isolate, may be transduced in the mixed populations by use of immobilized CD34 antibodies.

The cell surface binding molecules of the invention may target and bind any moiety found on the surface of the cell to be transduced. Preferably, the moieties are found as part of receptors, markers, or other proteinaceous or non-proteinaceous factors on the cell surface. The moieties include epitopes recognized by the cell surface binding molecule. These epitopes include those comprising a polypeptide sequence, a carbohydrate, a lipid, a nucleic acid, an ion and combinations thereof.

Examples of cell surface binding molecules include an antibody or an antigen binding fragment thereof and a ligand or binding domain for a cell surface receptor. The cell surface binding molecule may itself be a polypeptide, a nucleic acid, a carbohydrate, a lipid, or an ion. Preferably, the molecule is an antibody or a fragment thereof, such as a $F_{ab}$ or $F_v$ fragment. More preferably, the molecule is not used in a soluble form but is rather immobilized on a solid medium, such a bead, with which the cells to be transduced may be cultured, or the surface of a tissue culture dish, bag or plate, upon which the cells to be transduced may be cultured. In a preferred embodiment for the transduction of CD4+ or CD8+ cells, monoclonal antibodies that recognize CD3 and/or CD28 may be used in a cell culture bag in the presence of a viral vector.

The present invention includes compositions comprising a cell surface binding molecule for use as part of the disclosed methods. An exemplary composition comprises the molecule and a viral vector to be transduced, optionally in the presence of the cells to be transduced. The viral vectors may be derived from any source, but are preferably retroviral vectors. More preferably, they are lentiviral vectors. A particularly preferred lentiviral vector is one derived from a Human Immunodeficiency Virus (HIV), most preferably HIV-1, HIV-2, or chimeric combinations thereof. Of course different viral vectors may be simultaneously transduced into the same cell by use of the present methods. For example, one vector can be a replication deficient or conditionally replicating retroviral vector while a second vector can be a packaging construct that permits the first vector to be replicated/packaged and propagated. When various viral accessory proteins are to be encoded by a viral vector, they may be present in any one of the vectors being transduced into the cell. Alternatively, the viral accessory proteins may be present in the transduction process via their presence in the viral particles used for transduction. Such viral particles may have an effective amount of the accessory proteins co-packaged to result in an increase in transduction efficiency. In a preferred embodiment, the viral vector does not encode one or more of the accessory proteins.

A viral vector for use in the transduction methods of the invention can also comprise and express one or more nucleic acid sequences under the control of a promoter. In one embodiment of the invention, a nucleic acid sequence encodes a gene product that, upon expression, would alleviate or correct a genetic deficiency in the cell to be transduced. In another embodiment, the nucleic acid sequence encodes or constitutes a genetic antiviral agent that can prevent or treat viral infection. By "genetic antiviral agent", it is meant any substance that is encoded or constituted by genetic material. Examples of such agents are provided in U.S. Pat. No. 5,885,806. They include agents that function by inhibiting viral proteins, such as reverse transcriptase or proteases; competing with viral factors for binding or target sites; or targeting viral targets directly for degradation, such as in the case of ribozymes and antisense constructs. Other examples of genetic antiviral agents include antisense, RNA decoys, transdominant mutants, interferons, toxins, nucleic acids that modulate or modify RNA splicing, immunogens, and ribozymes, such as "hammerhead" and external guide sequence (EGS) mediated forms thereof.

Alternatively, a viral vector can encode a marker for transduced cells. In the examples presented in the figures and below, green fluorescent protein (GFP) is the marker encoded by the viral vector transduced into CD4+ cells. Other markers include those listed above. Detection of GFP may serve to identify the number of functionally transduced cells, which were not only transduced with the vector, but were also able to functionally express GFP to levels that could be detected by FACS analysis. It should be noted that the detection may not represent the actual number of transduced cells since some cells may have been transduced with the vector but express GFP at levels that are below the limits used in FACS detection.

An alternative approach to detecting transfection efficiency is with the polymerase chain reaction (PCR). For example, TaqMan PCR can be used to determine the actual number of copies of stably integrated viral vector in a transduced cell.

The cells to be transduced may be exposed to contact with the viral vector either before, after or simultaneously with contact with the cell surface binding molecule. Thus the cells can be first exposed to the vector for a period of time followed by introduction of the cell surface binding molecule. Such cells may be newly isolated or prepared primary cells that have not been intentionally stimulated to enter the cell cycle. Alternatively, the cells can be first exposed to the cell surface binding molecule for a period of time followed by contact with the viral vector. After contact with the vector, excess vector is preferably not removed and the cells cultured under conditions conducive to cell growth and/or proliferation. Such conditions may be in the presence of the cell surface binding molecule or other stimulatory/activating factors, such as cytokines and lymphokines in the case of T cells. Alternatively, excess vector may be removed after contact with the cell and before further culturing.

Another embodiment of the invention is to culture the cells in the presence of both viral vector and cell surface binding molecule simultaneously. Such cells are preferably not previously stimulated. After a period of time, the cells are cultured under growth or proliferation inducing conditions such as the continued presence of the cell surface binding molecule or other stimulatory/activating factors. Alternatively, excess vector may be removed before further culturing.

In any of the above combinations of viral vector and cell surface binding molecule administration, incubation with the vector can be optionally repeated at least once. Contact with the vector can also be repeated more than once, such as twice, thrice, four times, or more.

Incubation of the cells to be transduced with the viral vector may be for different lengths of time, depending on the conditions and materials used. Factors that influence the incubation time include the cell, vector and MOI (multiplicity of infection) used, the molecule(s) and amounts used to bind the cell surface, whether and how said molecule(s) are immobilized, and the level of transduction efficiency desired. In a preferred embodiment of the invention, the cells are T lymphocytes, the vector HIV based, the MOI is about 20, the cell surface binding molecules are CD3 and CD28 antibodies immobilized on beads, and the resultant efficiency at least 93%. As would be evident to the skilled person in the art, some of the above factors are directly correlated while others are inversely correlated. For example, a decrease in the MOI will likely decrease the level of efficiency while efficiency can likely be maintained if an increased amount of cell surface binding molecules is used.

The length of incubation viral vector and the cells to be transformed is preferably for 24 hours and optionally repeated once for lymphocytes and up to four times for hematopoietic stem cells. Similarly, and in embodiments where the cells are incubated with the cell surface binding molecule before introduction of the viral vector, the incubation may be for about 12 hours to about 96 hours. Preferably, incubation with a cell surface binding molecule occurs simultaneously with contact of the cells with the viral vector. Under such circumstances, the cell surface binding molecules may be left in contact with the cells when the vector is introduced. Alternatively, excess cell surface binding molecules may be first removed from the culture before introduction of the vector to the cells.

After contact with the vector, the cells are cultured under conditions conducive to their growth or proliferation. Preferably, the conditions are continued culturing in the presence of the cell surface binding molecules. Alternatively, the cells are initially cultured with the cell surface binding molecule followed by substitution with media containing another factor conducive to cell growth, such as interleukin-2. Yet another embodiment would be to remove both the excess cell surface binding molecule and the excess vector followed by culturing in the presence of a factor conducive to growth or proliferation as well as enhancing further vector transduction. Such factors include mitogens such as phytohemaglutinin (PHA) and cytokines, growth factors, activators, cell surface receptors, cell surface molecules, soluble factors, or combinations thereof, as well as active fragments of such molecules, alone or in combination with another protein or factor, or combinations thereof.

Examples of additional factors include epidermal growth factor (EGF), transforming growth factor alpha (TGF-alpha), angiotensin, transforming growth factor beta (TGF-beta), GDF, bone morphogenic protein (BMP), fibroblast growth factor (FGF acidic and basic), vascular endothelial growth factor (VEGF), PlGF, human growth hormone (HGH), bovine growth hormone (BGH), heregulins, amphiregulin, Ach receptor inducing activity (ARIA), RANTES (regulated on activation, normal T expressed and secreted), angiogenins, hepatocyte growth factor, tumor necrosis factor beta (TNF-beta), tumor necrosis factor alpha (TNF-alpha), angiopoietins 1 or 2, insulin, insulin growth factors I or II (IGF-I or IGF-2), ephrins, leptins, interleukins 1, 2, 3, 4, 5, 6, 7, 8, 9, 10, 11, 12, 13, 14, or 15 (IL-1, IL-2, IL-3, IL-4, L-5, IL-6, IL-7, IL-8, IL-9, IL-10, IL-11, IL-12, IL-13, IL-14, or IL-15), G-CSF (granulocyte colony stimulating factor), GM-CSF (granulocyte-macrophage colony stimulating factor), M-CSF (macrophage colony stimulating factor), LIF (leukemia inhibitory factor), angiostatin, oncostatin, erythropoietin (EPO), interferon alpha (including subtypes), interferons beta, gamma, and omega, chemokines, macrophage inflammatory protein-I alpha or beta (MIP-1 alpha or beta), monocyte chemotactic protein-1 or -2 (MCP-1 or 2), GRO beta, MWF (macrophage migration inhibitory factor), MGSA (melanoma growth stimulatory activity), alpha inhibin HGF, PD-ECGF, bFGF, lymphotoxin, Mullerian inhibiting substance, FAS ligand, osteogenic protein, pleiotrophin/midkine, ciliary neurotrophic factor, androgen induced growth factor, autocrine motility factor, hedgehog protein, estrogen, progesterone, androgen, glucocorticoid receptor, RAR/RXR, thyroid receptor, TRAP/CD40, EDF (erythroid differentiating factor), Fic (growth factor inducible chemokine), IL-1RA, SDF, NGR or RGD ligand, NGF, thymosine-alpha1, OSM, chemokine receptors, stem cell factor (SCF), or combinations thereof. As evident to one skilled in the art, the choice of culture conditions will depend on knowledge in the art concerning the cells transduced as well as the subsequent intended use of the cells. For example, the combination of IL-3, IL-6 and stem cell factor would not be a choice for transduced cells that are to be used in human transplantation. Similarly, the choice of culture conditions would preferably not be to the detriment of cell viability or transduction efficiency.

Preferably, the post transduction incubation is for a period of about four hours, or for about one to about seven to ten days. More preferably from about 16 to about 20 hours or for about four, about five or about six days. About fourteen days of post-transduction incubation is also contemplated.

The efficiency of transduction observed with the present invention is from about 75–100%. Preferably, the efficiency is at least about 75 to 90%. More preferred embodiments of the invention are where transduction efficiency is at least about 90 to 95%. The most preferred embodiments have transduction efficiencies of at least 91, 92, 93, 94, 95, 96, 97, 98, 99 and 100%.

In addition to the above, the transduced cells may be used in research or for treatment of disease conditions in living subjects. Particularly preferred as part of the invention are therapeutic uses for the transduced cells to produce gene products of interest or for direct introduction into a living organism as part of gene therapy. For example, and as exemplified below, primary T cells can be isolated and transduced with a viral vector. Successful transduction is indicated by the production or overproduction of a gene product encoded by the vector or generation of a phenotype conferred by the vector. As such, primary T cells can be first transduced with a vector containing, and capable of expressing, desirable or useful nucleic acid sequences, and then returned to an in vivo environment such as a living subject. Preferably, the living subject is an individual infected with, or at risk of being infected with HIV-1.

In another embodiment, the T cells are transduced with genes or nucleic acids capable of conditionally killing the T cell upon introduction into a host organism. This has applications in allogenic bone marrow transplantation to prevent graft versus host disease by killing T cells with a pro-drug approach.

Alternatively, the primary cells can be deficient in a gene product, and the deficiency correctable by the transduced viral vector. Such cells would be reintroduced into the living subject after transduction with the vector.

Thus, both in vitro and ex vivo applications of the invention are contemplated. For transfers into a living subject, the transduced cells are preferably in a biologically acceptable solution or pharmaceutically acceptable formulation. Such a transfer may be made intravenously, intraperitoneally or by other injection and non-injection methods known in the art. The dosages to be administered will vary depending on a variety of factors, but may be readily determined by the skilled practitioner. There are numerous applications of the present invention, with known or well designed payloads in the viral vector, where the benefits conferred by the transduced genetic material will outweigh any risk of negative effects.

Initially, the total number of transduced cells transferred would be from about 104 to about $10^{10}$. As such, $10^5$, $10^6$, $10^7$, $10^8$, or $10^9$ cells may be used. The actual numbers will vary depending on the cells being transduced. Multiple transfers, if required, of transduced cells are a preferable embodiment. Furthermore, conditioning of the host prior to the transfer of transduced cells, if required, is a preferable embodiment. Conditioning regimens are known in the art; an example is the regimen(s) for bone marrow transplantation.

Having now generally described the invention, the same will be more readily understood through reference to the following examples which are provided by way of illustration, and are not intended to be limiting of the present invention, unless specified.

EXAMPLE I

Preparation of Primary CD4+ T Cells

CD4+ T cells were isolated from peripheral blood using standard protocols with slight modification. More specifically, contaminating monocytes were depleted by attachment. Non adherent cells were placed in the presence of magnetic beads coated with anti-CD4 antibodies for positive selection of CD4+ cells. The magnetic beads were removed and CD4+ cells isolated.

The highly purified CD4+ cells were confirmed to be greater than 90% by flow cytometry.

EXAMPLE II

Figure 1B:
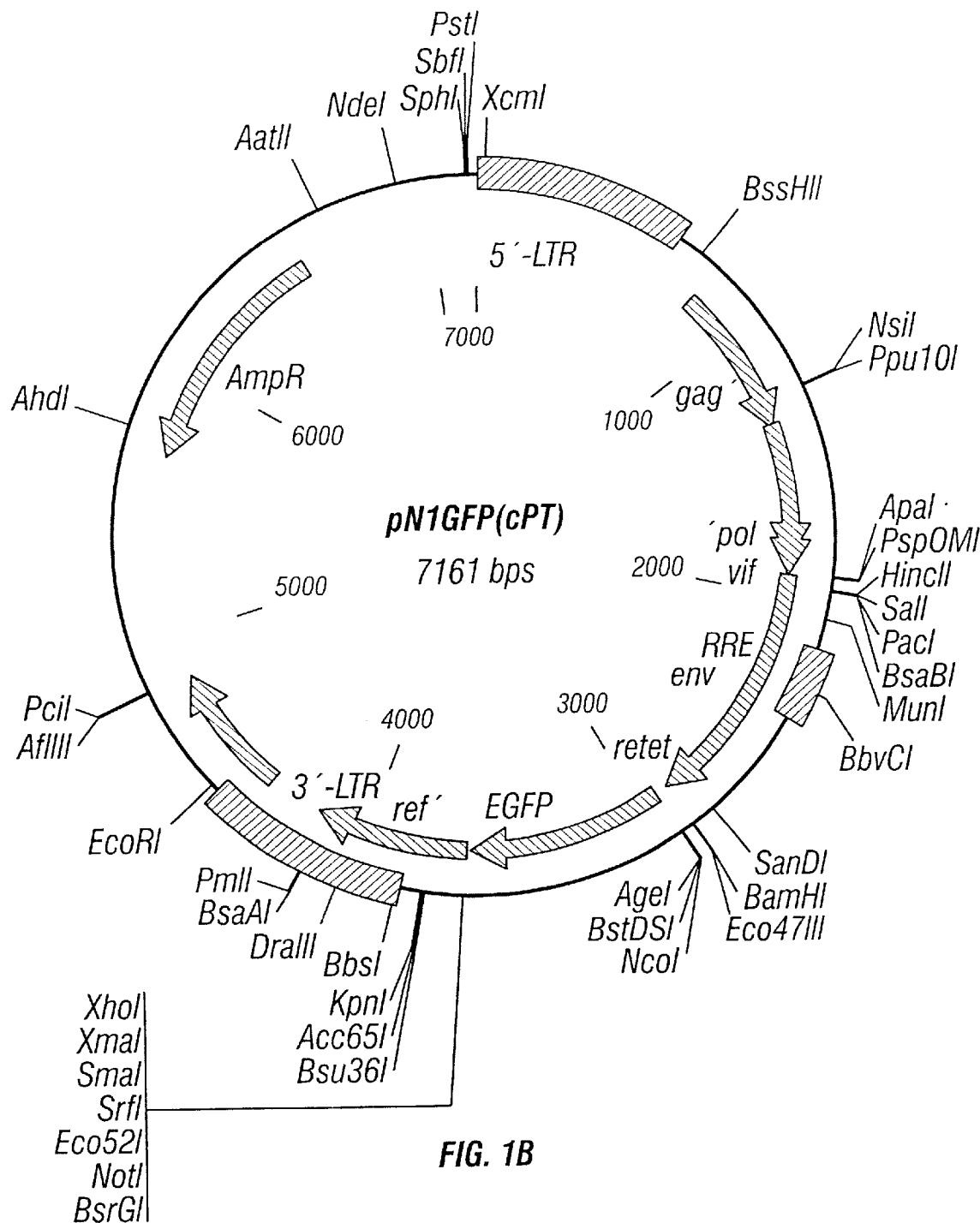

Transduction of Primary CD4+ T Cells With Variations in Time of Contact With a Cell Surface Binding Molecule Transduction Before Cell Surface Binding Primary CD4+ cells (about 500,000) were cultured with pN2cGFP at a MOI of 20 for 24 hours followed by addition of αCD3 and αCD28 coated beads to the culture for an additional seven days. FIG. 1 contains a map of pN2cGFP.
Transduction After Cell Surface Binding Primary CD4+ cells (about 500,000) were cultured for 24 hours with αCD3 and αCD28 coated beads for 24 hours followed by introduction of pN2cGFP at a MOI of 20 to the culture for an additional 24 hours. The cells were washed to remove excess vector followed by incubation in vector free media containing the beads for an additional seven days.
Simultaneous Transduction and Cell Surface Binding Primary CD4+ cells (about 500,000) were cultured with pN2cGFP at a MOI of 20 for 24 hours in the presence of αCD3 and αCD28 coated beads. The cells were washed to remove excess vector followed by incubation in vector free media containing the beads for an additional seven days.
Optional Protocol Substitutions Other viral vectors may be substituted for pN2cGFP. Additionally, the transduction may be repeated for a total of two times prior to removal of excess vector. Moreover, the αCD3 and αCD28 coated beads may be substituted by interleukin-2 (10 ng/ml) and PHA-P (3 mg/ml) after transduction and removal of excess vector. After seven days, the media is replace with PHA-P free media containing interleukin-2 (10 ng/ml) and the incubation continued for an additional seven days.

Alternatively, after seven days of post-transduction incubation with αCD3 and αCD28 coated beads, the cells are washed and incubation continued in the presence of interleukin-2 (10 ng/ml).

EXAMPLE III

Post-transduction Analysis

Post-transduction and seven or 14 days after incubation, the cells were analyzed by flow cytometry for CD4+ and/or green fluorescent protein (GFP).

Figure 2A:
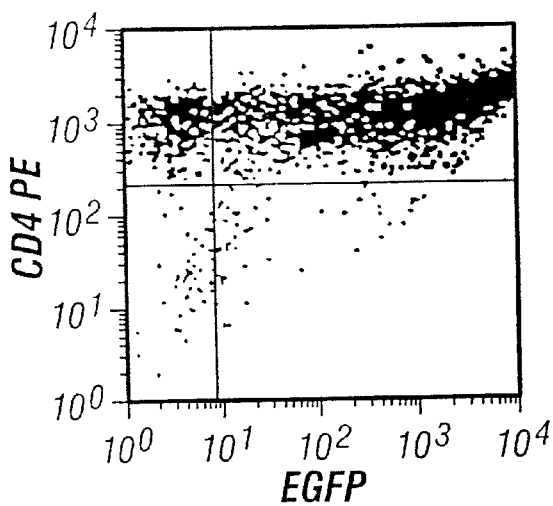
FIGS. 2A, 2B and 2C show the results of transduction of primary T cells using beads coated with immobilized CD3 and CD28 antibodies. The cells were either contacted with vector before contact with the beads (Panel A), contacted with the beads prior to contact with the vector (Panel B), or simultaneously contacted with both vector and beads (Panel C). The flow cytometry results based on fluorescence from GFP encoded by the transduced vector indicate that the cells in Panels A–C were transduced 90.70, 87.19, and 79.14%, respectively.
Figure 2B:
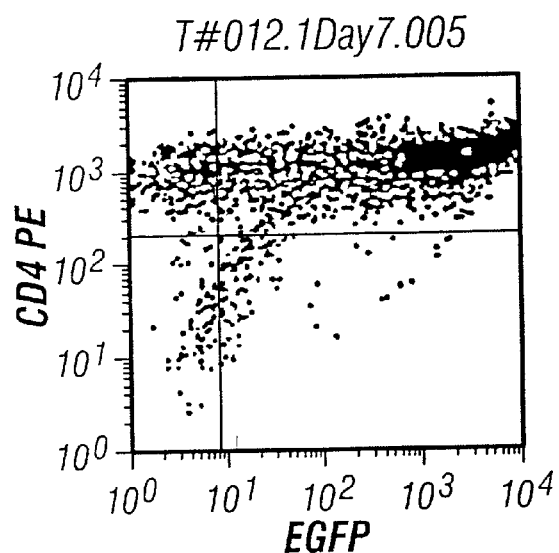
Figure 2C:
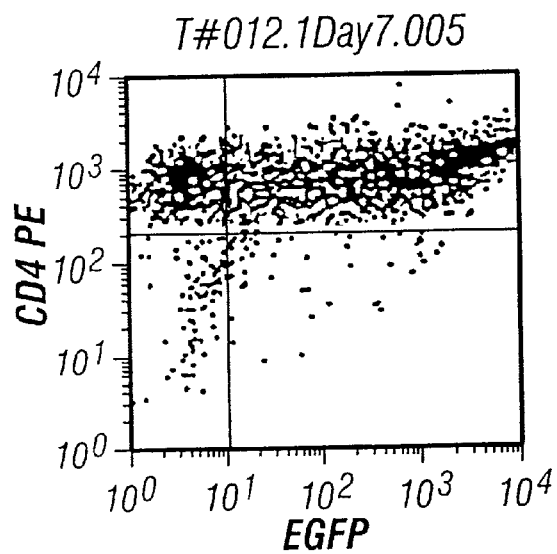
Figure 3A:
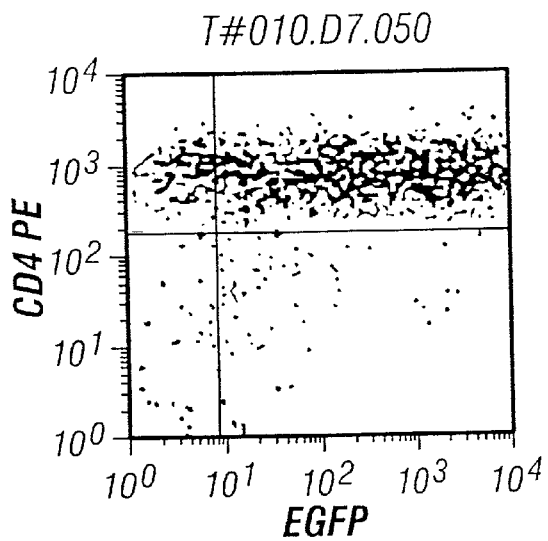
FIGS. 3A, 3B, 3C, 3D, 3E and 3F show a comparison of transduction using either IL-2 and PHA-P or bead immobilized CD3 and CD28 antibodies to stimulate CD4+ cells before contact with viral vector. The use of immobilized antibodies resulted in transduction efficiencies of over 95% each time. The use of IL-2 and PHA resulted on efficiencies of only 70.2 to 84.5%.
Figure 3B:
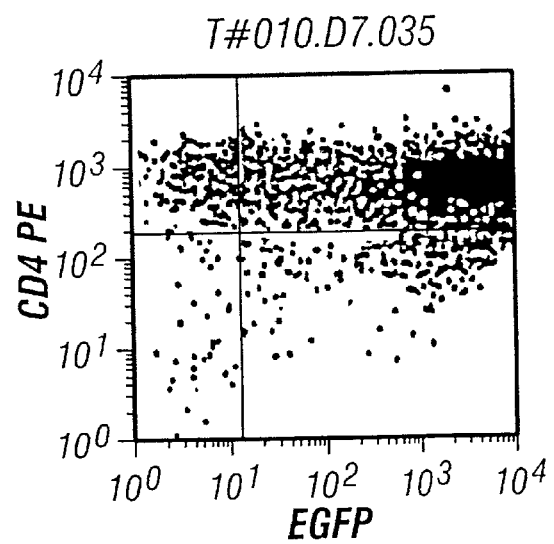
Figure 3C:
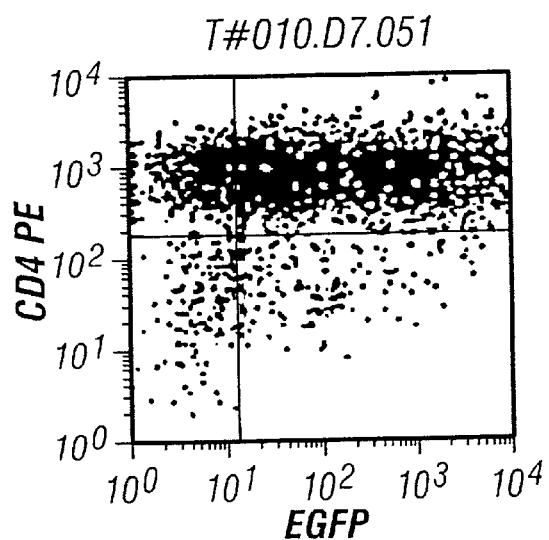
Figure 3D:
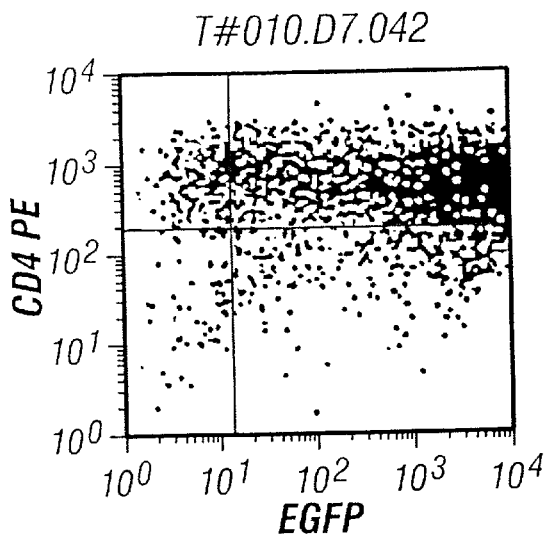
Figure 3E:
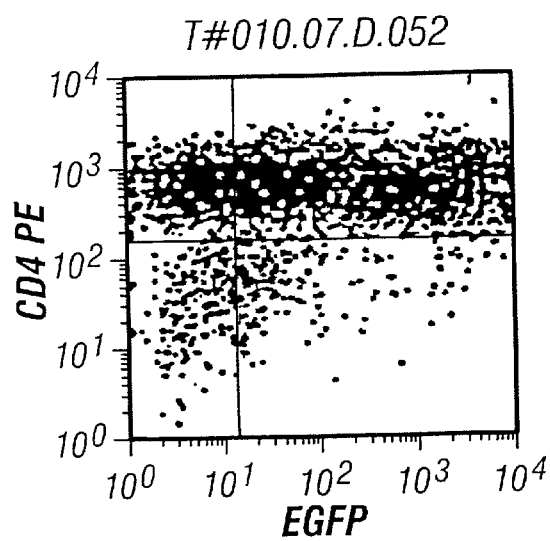
Figure 3F:
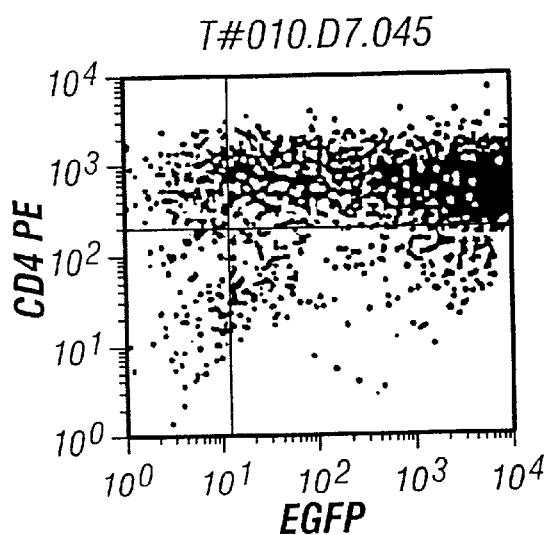

A comparison of the above three transduction protocols is shown in FIG. 2. Contact with bead immobilized CD3 and CD28 antibodies after transduction with pN2cGFP at an MOI of 20 resulted in about 91% efficiency. Contact with beads before transduction resulted in about 89% efficiency, and simultaneous bead contact and transduction resulted in about 80% efficiency. In this experiment, the CD4+ T cells were selected by adherence monocyte depletion, CD14 MACS depletion and CD4 MACS enrichment. The antibodies were immobilized as described below. Contact with the vector was at 37° C. and 5% $CO_2$. The culture conditions were at 500,000 CD4+ T cells per ml in Yssel's medium supplemented with 2% human serum albumin. FACS analysis was on day seven post selection. MF refers to mean fluorescence.

The results for an experiment after seven days comparing different stimulation conditions are shown in FIG. 3. CD4+ cells were treated with either IL-2 and PHA-P or bead immobilized CD3 and CD28 antibodies for 24 hours followed by one round of transduction with pN2cGFP at an MOI of 20. In side by side comparisons, the use of immobilized antibodies resulted in transduction efficiencies of over 95% each time (indicated by cells positive for both CD4 and GFP). By comparison, the results with IL-2 and PHA stimulation resulted on efficiencies of only 70.2 to 84.5%. FACS analysis was on day seven post selection.

Figure 4A:
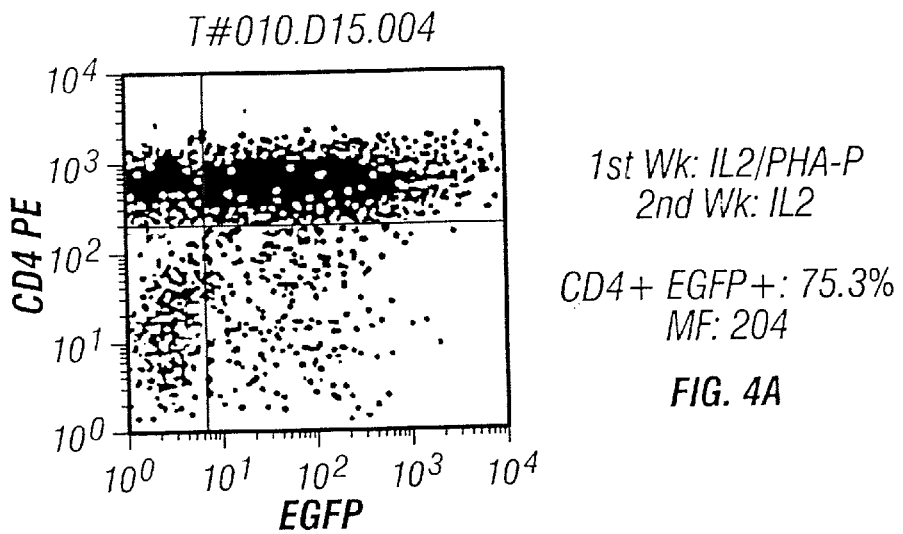
FIGS. 4A and 4B are a depiction of the frequency of human CD4+ T cell transduction using the present methods. Fifteen days post transduction, a comparison of flow cytometry analysis of control cells versus cells transduced with a vector capable of expressing green fluorescent protein (GFP) at a MOI of 20 shows that about 93% of the transduced cells also exhibit green fluorescence.
Figure 4B:
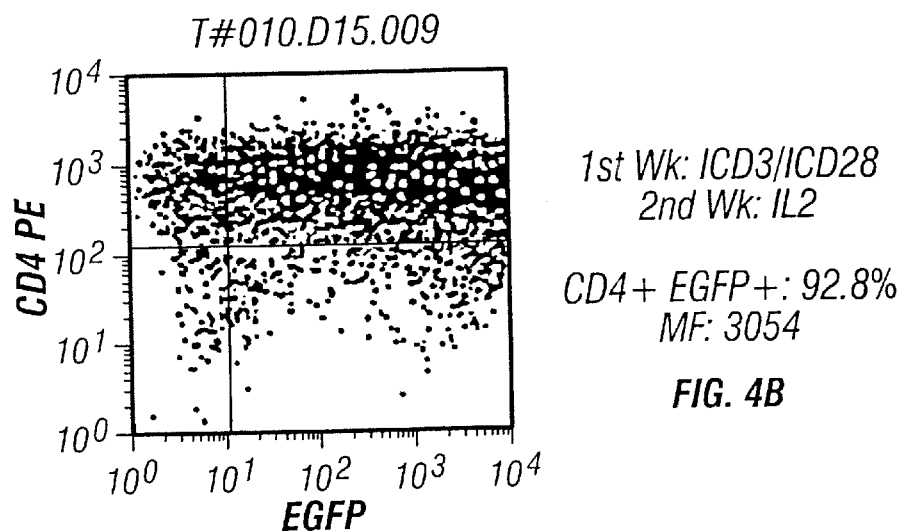

FIG. 4 shows the results of a similar experiment at 15 days post selection. Cells were again treated with either IL-2 and PHA-P or bead immobilized CD3 and CD28 antibodies for 24 hours followed by one round of transduction with pN2cGFP at an MOI of 20. The PHA-P and beads were removed on day 7 after transduction, and the cells were cultured with only IL-2 at 500,000 cells per ml. until day 15 post selection. Approximately 93% of the cells were positive for both CD4 and GFP after the use of immobilized antibodies. Only about 75% of cells treated with IL-2 and PHA remained positive for both CD4 and GFP. These results indicate that a small fraction of the cells detected as positive after seven days (FIG. 3) may have been due to "pseudotransfection."

EXAMPLE IV

Different Vectors Stably Transduce Cells at High Efficiencies

Figure 5A:
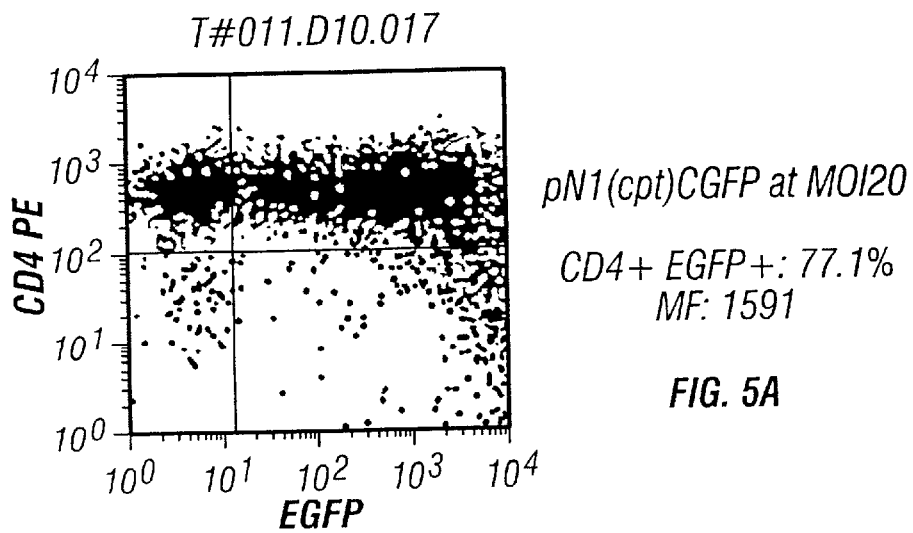
FIGS. 5A and 5B show the results of cells transduced with different viral vectors.
Figure 5B:
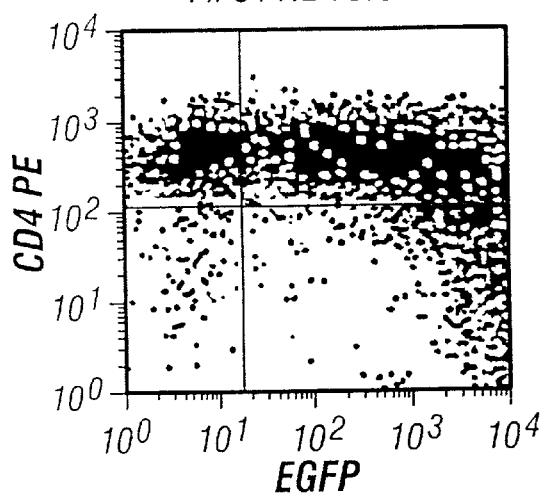
Figure 6A:
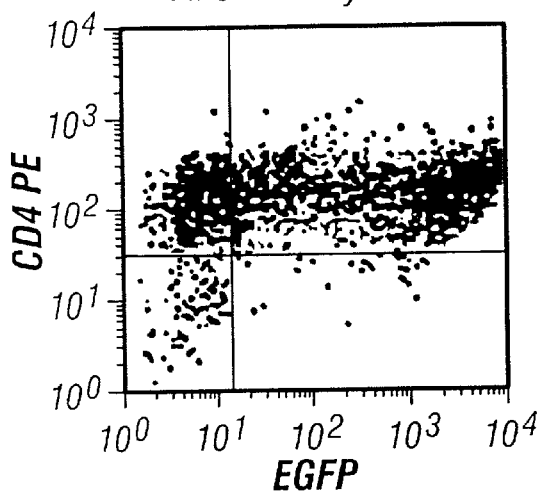
FIGS. 6A, 6B, 6C, 6D and 6E show the effect from the use of different MOIs on transfection efficiency.
Figure 6B:
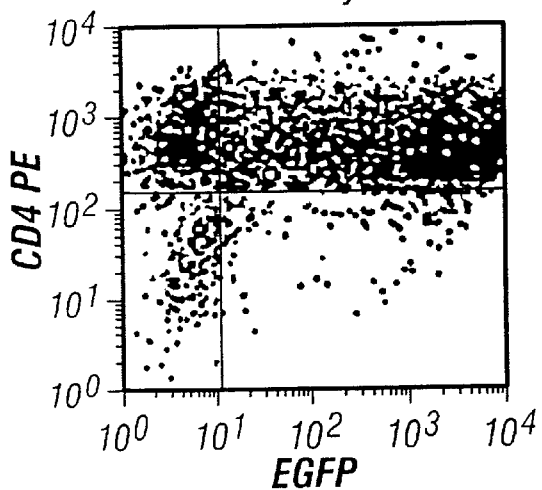
Figure 6C:
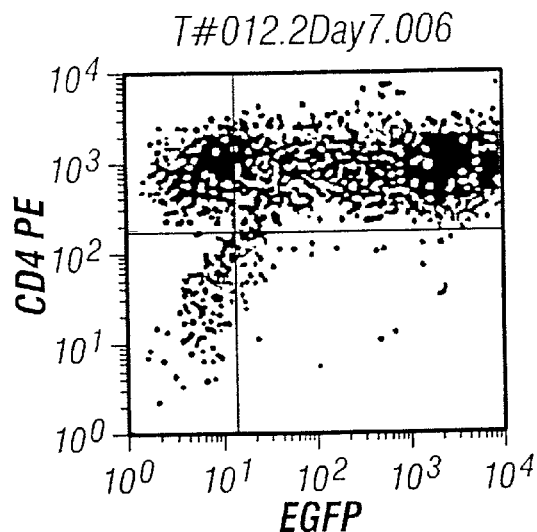
Figure 6D:
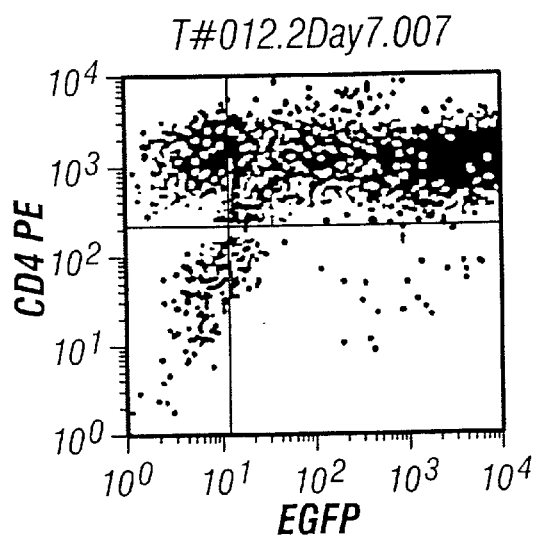
Figure 6E:
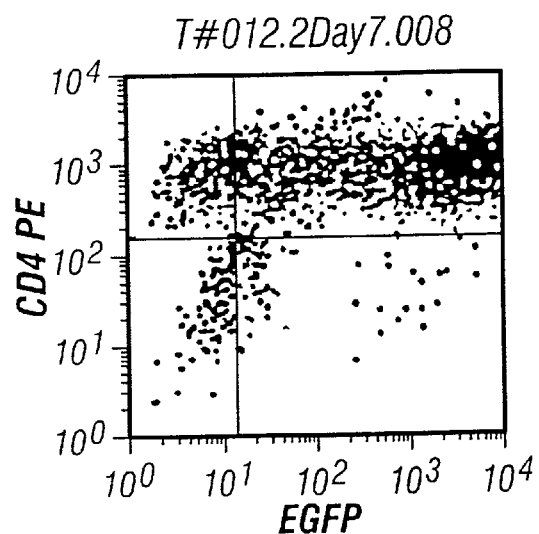

This example is a comparison of vectors used for transduction. pN2cGFP contains the entire gag and pol coding sequence while pN1(cpt)cGFP contains the 4551–5096 partial (non-coding) pol sequence. As can be seen from the results, shown in FIG. 5, both vectors show very efficient transduction of primary CD4 cells after simultaneous stimulation with bead immobilized CD3 and CD28 antibodies and vector at an MOI of 20. FACS analysis was performed on day 10 post selection.

EXAMPLE V

Effect of MOI on Transfection Efficiency

The effect of different MOIs are shown in FIG. 6, where the use of MOIs from 2 to 20 resulted in transduction efficiencies from 72.7 to 83.8%. Cells were contacted with bead immobilized CD3 and CD28 antibodies for 24 hours before transduction with pN1(cpt)CGFP at different MOIs.

EXAMPLE VI

Transduction of CD34 Positive Cells

CD34 positive cells were prepared from cord blood and transduced four times with pN1cptGFP simultaneously in the presence of FLT-3 ligand, TPO and Kit ligand (100 ng/ml each). The cells were cultured for five weeks in long term culture (LTC-IC) and then the cells cultured in methylcellulose for 10 days prior to analysis (the results are from an elapsed time of over 6 weeks in culture). The results in FIG. 7 analyze mature CD45 positive cells that result from the CD34 immature cells. Control cells show no significant transduction while the vector transduced cells show over 88% of cells as CD45 and GFP positive.

EXAMPLE VII

Long Term Transduction of CD34 Positive Cells

Figure 7A:
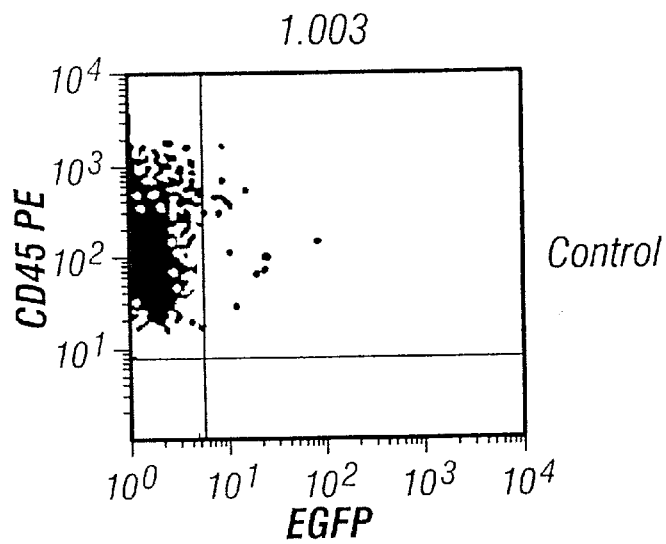
FIGS. 7A and 7B demonstrate the stable transduction of CD34+ cells prepared from umbilical cord blood after multiple transductions with a viral vector in the presence of cell surface binding molecules. Over 88% of cells remained positive after over 6 weeks post transduction
Figure 7B:
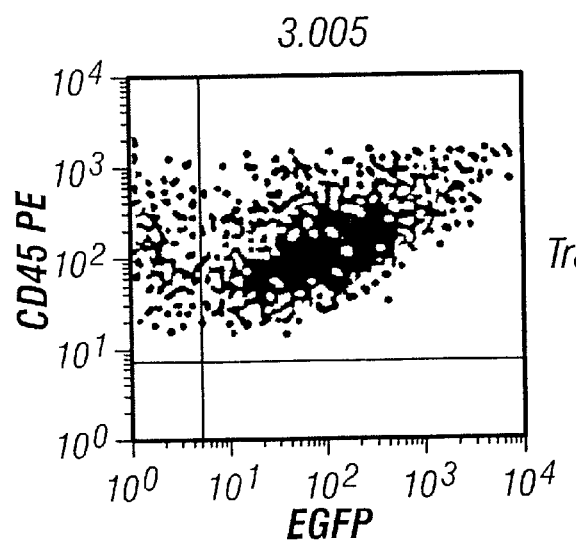
Figure 8A:
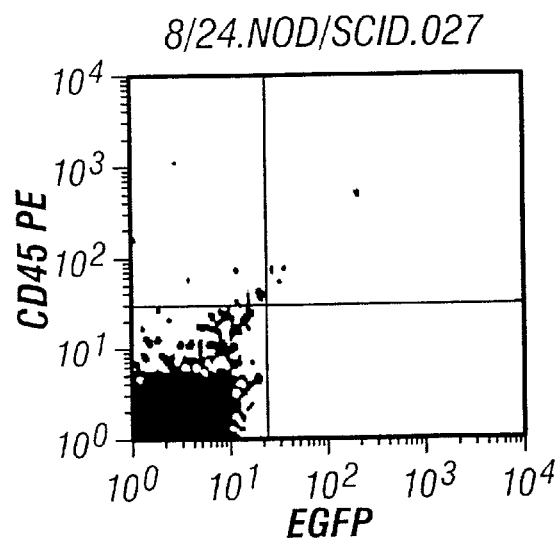
FIGS. 8A, 8B, 8C and 8D show the efficiency of long term transduction after transplantation to SCID (severe combined immunodeficiency) mice. After approximately eight weeks, an average of over 91% of the-transduced cells, which continued to mature, remained positive for expression of the transduced GFP marker.
Figure 8B:
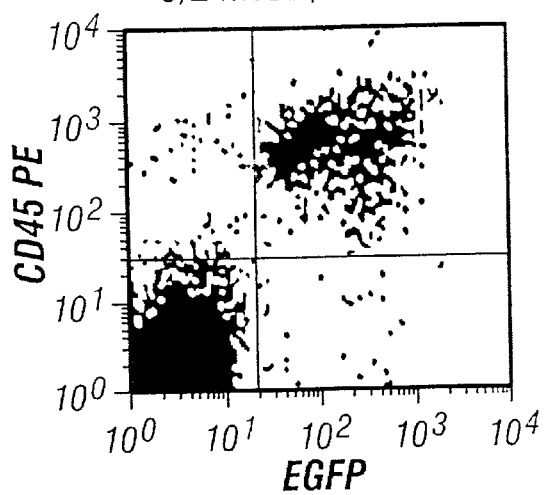
Figure 8C:
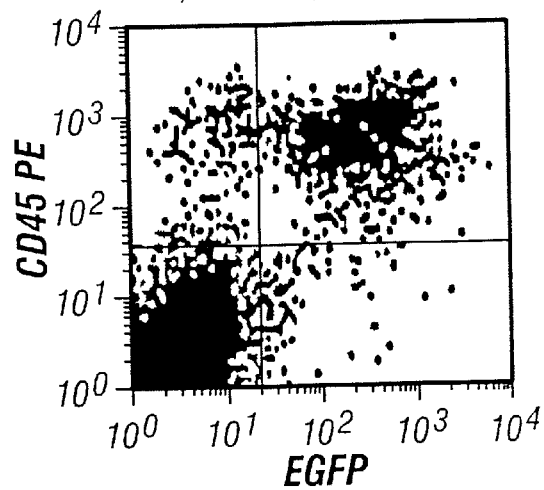
Figure 8D:
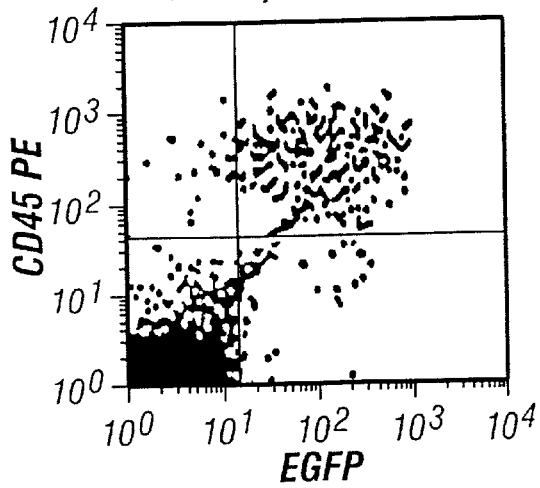

CD34 positive cells were transduced with pN1(cpt)GFP as described above and transplanted to the bone marrow of partially irradiated SCID mice. After eight weeks, cells were isolated and analyzed for CD45 bearing mature human cells and GFP expression by FACS. The results are shown in FIG. 7, panels A to D.

Panel A shows the results with a control mouse transplanted with human cells not transduced with vector.

Panel B shows the results with a mouse transplanted with cells transduced with cells transduced with pN1(cpt)GFP vector at a MOI of 50 for 4 sequential days in the presence of 10 ng/ml of FLT-3 ligand, TPO and Kit ligand. This mouse shows a striking 96.3% transduction efficiency of transduced human cells (CD45 positive cells) 8 weeks after transduction. The level of human cell engraftment in this mouse was 11.1%, consistent with previously reported results.

Panels C and D show the results with two other mice treated as in panel B. The results confirm reproducibility of high efficiency transduction with 87.8% and 89.6% of CD45 positive cells also being GFP positive.

The average efficiency is 91.2%, which reflects long term stable transduction.

EXAMPLE VIII

Immobilization of Cell Surface Binding Molecules

This example describes the direct linkage of CD3 (B-B11) antibodies and CD28 (B-T3) antibodies to epoxy dynal beads for use in the examples below.

1. Prepare 0.1 borate solution by dissolving 0.618 g. boric acid in 95 ml of tissue culture grade water. Mix well and adjust pH to 9.5 using highest quality NaOH. Bring final volume to 100 ml and sterilize via a 0.2 $\mu$m filter. Seal container and store at 4° C.
2. Add antibody to above borate solution at a concentration of 150 $\mu$g/ml. For both B-B 11 and B-T3 antibodies, add 75 $\mu$g of each per ml of borate solution. Bring volume to 1 ml total. Borate concentration should not be below 0.05 M after adding antibody. For each 1 ml of borate/antibody solution, add $4 \times 10^8$ Epoxy beads.
3. Incubate 24 hours at 37° C. on rotating wheel.
4. Wash beads three times for 10 min. each at 22° C. with bead wash media: phosphate buffered saline without calcium and magnesium, 3% human serum albumin, 5 mM EDTA, and 0.1 sodium azide.
5. Wash beads once for 30 min at 22° C.
6. Wash overnight at 4° C.
7. Replace with fresh bead wash media, resuspend beads to $2 \times 10^8$ beads/ml. IgG coated beads are stable for at least 6 months at 4° C.

EXAMPLE IX

Transduction of Dendritic Cells

Figure 9A:
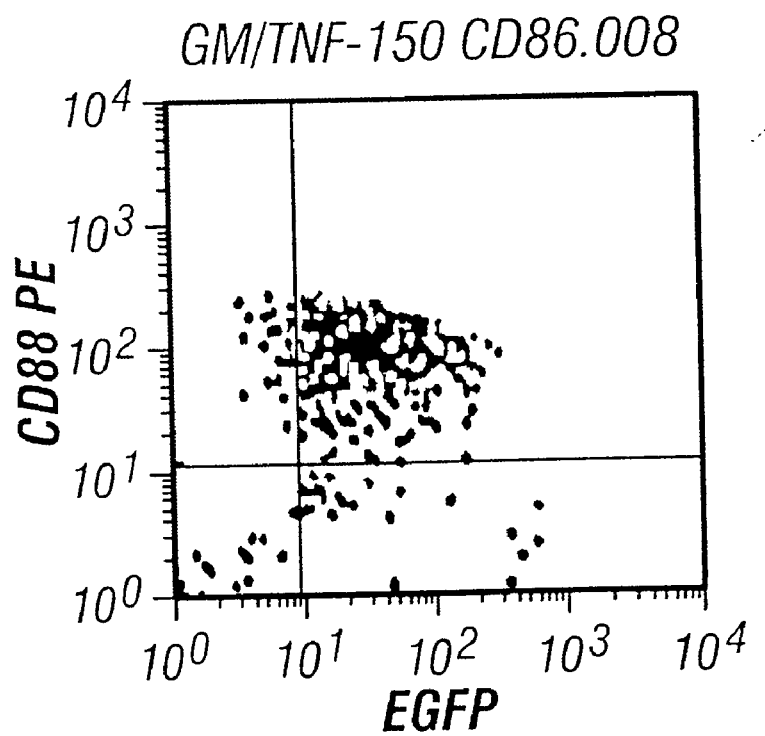
FIGS. 9A and 9B show the efficiency of dendritic cell transduction after seven days.
Figure 9B:
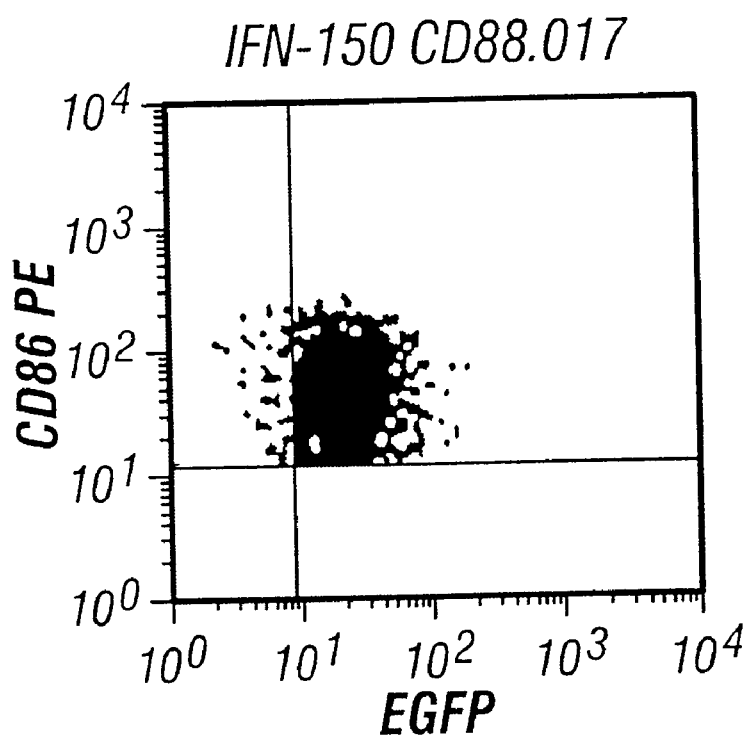

Monocytes from peripheral blood were isolated and then transduced for three consecutive days at an MOI of 50 with pN2cGFP using two simultaneous cytokine conditions: GM-CSF (800 units/ml), IL-4 (500 units/ml) and TNF-alpha (100 units/ml) or GM-CSF (500 units/ml) and interferon-alpha (800 units/ml). FIG. 9, panel A, shows the results seven days post transduction where the first cytokine condition resulted in 90.2% efficiency. Cells transduced with vector under the second cytokine conditions show a 92.9% efficiency after seven days (panel B). CD86 is only one possible marker for dendritic cells, and it should be noted that CD86 negative cells can also be dendritic cells.

References

Barry, S. C. et al. (2000) "Lentiviral and murine retroviral transduction of T cells for expression of human CD40 ligand" *Human Gene Therapy* 11:323–332.

Costello, E. et al. (2000) "Gene transfer into stimulated and unstimulated T lymphocytes by HIV-1-derived lentiviral vectors" *Gene Therapy* 7:596–604.

Douglas, J. et al. (1999) "Efficient transduction of human lymphocytes and CD34+ cells via human immunodeficiency virus-based gene transfer vectors" *Human Gene Therapy* 10:935–945.

Follenzi, A. et al. (2000) "Gene transfer by lentiviral vectors is limited by nuclear translocation and rescued by HIV-1 pol sequences" *Nature Genetics* 25:217–222.

Han, W. et al. (2000) "A soluble form of human Delta-like-1 inhibits differentiation of hematopoietic progenitor cells" *Blood* 95:1616–1625.

Haas, D. L., et al. (2000) "Critical factors influencing stable transduction of human CD34+ cells with HIV-1-derived lentiviral vectors" *Molecular Therapy* 2:71–80.

Hooijberg E. et al. (2000) "NFAT-controlled expression of GFP permits visualization and isolation of antigen-stimulated primary human T cells" *Blood* 96:459–466.

Kishimoto, T. (ed). Leucocyte Typing VI: White Cell Differentiation Antigens: Proceedings of the Sixth International Workshop and Conference Held in Kobe, Japan, Nov. 10–14, 1996. Garland Publishing, New York, 1998.

Klebba, C. et al. (2000) "Retrovirally expressed anti-HIV ribozymes confer a selective survival advantage on CD4+ T cells in vitro" *Gene Therapy* 7:408–416.

Koc, O. N., et al. (1999) "Transfer of drug resistance genes into hematopoietic progenitors" Chapter 11, *Gene Therapy of Cancer*, Academic Press, San Diego, pp. 177–195.

Movassagh, M. et al. (2000) "Retrovirus-mediated gene transfer into T cells: 95% transduction efficiency without further in vitro selection" *Human Gene Therapy* 11:1189–1200.

Onodera, M. et al. (1998) "Successful peripheral T-lymphocyte-directed gene transfer for a patient with severe combined immune deficiency caused by adenosine deaminase deficiency" *Blood* 91:30–36.

St. Croix, B., et al. (2000) "Genes expressed in human tumor endothelium" *Science* 289:1197–1202.

Unutmaz, D. et al. (1999) "Cytokine signals are sufficient for HIV-1 infection of resting human T lymphocytes" *J. Exp. Med.* 11:1735–1746.

Zennou, V., et al. (2000) "HIV-1 genome Nuclear import is mediated by a central DNA flap" *Cell* 101:173–185.

All references cited herein are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features herein before set forth as follows in the scope of the appended claims.

Hereinabove and in the claims below, use of the terms "a" or "an" is not limited to defining the singular state. Instead, use of the terms encompasses the plural state. For example the term "an antibody" is not limited to the singular state of one single antibody molecule, but rather encompasses the presence of a plurality of antibody molecules so long as they are identical copies of the antibody being referred to. Similarly, "a viral vector" is not limited to one single viral vector molecule or one single viral particle.

What is claimed is:

1. A method for stable transduction of primary cells of the hematopoietic system and/or hematopoietic stem cells comprising contacting the surface of said cells with both an HIV derived lentiviral vector and at least one molecule which binds said cell surface
   wherein said contacting occurs in vitro or ex vivo and
   wherein greater than about 90% of the cells are stably transduced after about 14 days.

2. The method of claim 1 wherein said contacting the cells with a lentiviral vector occurs before contacting the cells with at least one cell surface binding molecule.

3. The method of claim 1 wherein said contacting the cells with a lentiviral vector occurs simultaneously with contacting the cells with at least one cell surface binding molecule.

4. The method of claim 1 wherein said contacting the cells with a lentiviral vector occurs after contacting the cells with at least one cell surface binding molecule.

5. The method of claim 1 where said contacting with a lentiviral vector occurs more than once.

6. The method of claim 1 wherein said cell surface binding molecule is an antibody, a ligand or a cell surface molecule.

7. The method of claim 1 wherein said lentiviral vector comprises at least one cis-acting nucleotide sequence derived from the gag, pol, env, vif, vpr, vpu, tat or rev genes.

8. The method of claim 7 wherein said sequence is not expressed or is a fragment or a mutant of the gag, pol, env, vif, vpr, vpu, tat or rev genes.

9. The method of claim 1 wherein said lentiviral vector is a pseudotyped vector.

10. The method of claim 9 wherein said pseudotyped vector contains the vesicular stomatitis virus G envelope protein.

11. The method of claim 1 wherein said hematopoietic cell is a CD4 positive cell.

12. The method of claim 1 wherein said hematopoietic cell is a lymphocyte.

13. The method of claim 12 wherein said lymphocyte is a CD4 or CD8 positive cell.

14. The method of claim 1 wherein said hematopoietic cell is a CD34 positive cell.

15. The method of claim 14 wherein said at least one cell surface binding molecule comprises a molecule selected from FLT-3 ligand, TPO ligand, Kit ligand, or antibodies that are cell surface binding analogs of FLT-3 ligand, TPO ligand, or Kit ligand.

16. The method of claim 1 wherein said at least one cell surface binding molecule comprises a molecule selected from FLT-3 ligand, TPO ligand, Kit ligand, or antibodies that are cell surface binding analogs of FLT-3 ligand, TPO ligand, or Kit ligand.

17. The method of claim 1 wherein the said cell is a dendritic cell or a cell capable of differentiating into a dendritic cell.

18. The method of claim 17 wherein said at least one cell surface binding molecule is selected from compositions comprising GM-CSF, IL-4, and TNF-alpha; GM-CSF and interferon-alpha; or antibodies that are cell surface binding analogs of GM-CSF, IL-4, and TNF-alpha; GM-CSF or interferon-alpha.

19. The method of claim 11 wherein said at least one cell surface binding molecule is selected from the group consisting of CD3 antibodies and fragments thereof, CD28 antibodies and fragments thereof, and combinations of said antibodies and fragments thereof.

20. The method of claim 19 wherein said at least one cell surface binding molecule comprises a combination of CD3 and CD28 antibodies immobilized on coated beads.

21. The method of claim 3 further comprising culturing the cells under conditions conducive to growth and/or proliferation.

22. The method of claim 21 wherein said conditions comprise further incubation with a cell surface binding molecule or a cytokine.

23. The method of claim 22 wherein said cytokine is interleukin-2.

24. The method of claim 21 wherein said culturing is for about seven days.

25. The method of claim 21 wherein said culturing is for about 14 days.

26. The method of claim 3 wherein said contacting the cells with a lentiviral vector is for about 24 hours and is optionally repeated at least once.

27. The method of claim 1 wherein the lentiviral vector is present at an MOI of less than 500.

28. A method to introduce genetic material into a living subject comprising introduction of a cell transduced by the method of claim 1.

29. The method of claim 4 further comprising culturing the cells under conditions conducive to growth and/or proliferation.

30. The method of claim 1 wherein said contacting occurs ex vivo.

* * * * *